US012589090B2

(12) United States Patent
Sucholeiki

(10) Patent No.: US 12,589,090 B2
(45) Date of Patent: Mar. 31, 2026

(54) COMPOUNDS AND METHODS FOR THE TREATMENT OF DEGENERATIVE DISORDERS

(71) Applicant: Aquilus Pharmaceuticals, Inc., Winchester, MA (US)

(72) Inventor: Irving Sucholeiki, Winchester, MA (US)

(73) Assignee: Aquilus Pharmaceuticals, Inc., Winchester, MA (US)

( * ) Notice: Subject to any disclaimer, the term of this patent is extended or adjusted under 35 U.S.C. 154(b) by 926 days.

(21) Appl. No.: 17/310,044

(22) PCT Filed: Jan. 21, 2020

(86) PCT No.: PCT/US2020/014326

§ 371 (c)(1),
(2) Date: Jul. 13, 2021

(87) PCT Pub. No.: WO2020/154243

PCT Pub. Date: Jul. 30, 2020

(65) Prior Publication Data

US 2022/0047550 A1 Feb. 17, 2022

Related U.S. Application Data

(60) Provisional application No. 62/796,242, filed on Jan. 24, 2019.

(51) Int. Cl.

| | |
|---|---|
| ***A61K 31/404*** | (2006.01) |
| ***A61K 45/06*** | (2006.01) |
| ***A61P 1/00*** | (2006.01) |
| ***A61P 25/02*** | (2006.01) |
| ***A61P 25/28*** | (2006.01) |
| ***C07D 409/12*** | (2006.01) |

(52) U.S. Cl.

CPC ............ *A61K 31/404* (2013.01); *A61K 45/06* (2013.01); *A61P 1/00* (2018.01); *A61P 25/02* (2018.01); *A61P 25/28* (2018.01); *C07D 409/12* (2013.01)

(58) Field of Classification Search

CPC ................ A61K 31/381; A61K 31/404; A61K 31/4436; A61P 25/28; C07D 409/12

See application file for complete search history.

(56) References Cited

FOREIGN PATENT DOCUMENTS

WO WO-2010075287 A2 * 7/2010 .......... A61K 31/381

OTHER PUBLICATIONS

Cribbs et al., Commentary: Caspase-Mediated Degeneration in Alzheimer's Disease, American Journal of Pathology, vol. 165, No. 2, pp. 353-355 (2004).*

Renaud et al., Matrix Metalloproteinases in neuromuscular disease—Abstract, Muscle Nerve (2007).*

Cribbs et al., Commentary: Caspase-Mediated Degeneration in Alzheimer's Disease, American Journal of Pathology, vol. 165, No. 2, pp. 353-355 (2004). (Year: 2004).*

Renaud et al., Matrix Metalloproteinases in neuromuscular disease—Abstract, Muscle Nerve (2007). (Year: 2007).*

Renaud et al., Matrix Metalloproteinases in neuromuscular disease, 2007, Muscle Nerve, 36, pp. 1-13 (2007). (Year: 2007).*

Liedtke et al., "Effective Treatment of Models of Multiple Sclerosis by Matrix Metalloproteinase Inhibitors", 1998, Annals of Neurology, 44, pp. 35-46 (Year: 1998).*

Marshall et al., "Selective Allosteric Inhibition of MMP9 Is Efficacious in Preclinical Models of Ulcerative Colitis and Colorectal Cancer", 2015, PLOS one, 10, pp. 1-26 (Year: 2015).*

Li et al., "Matrix metalloproteinase-9 inhibition ameliorates pathogenesis and improves skeletal muscle regeneration in muscular dystrophy", 2009, Human Molecular Genetics, 18, pp. 2564-2598 (Year: 2009).*

Khan et al., "Implication of Caspase-3 as a Common Therapeutic Target for Multineurodegenerative Disorders and Its Inhibition Using Nonpeptidyl Natural Compounds", 2015, BioMed Research International, pp. 1-9 (Year: 2015).*

Lee et al., "Induction of Caspase-Mediated Cell Death by Matrix Metalloproteinases in Cerebral Endothelial Cells After Hypoxia-Reoxygenation", 2004, Journal of Cerebral Blood Flow & Metabolism, vol. 24, pp. 720-727 (Year: 2004).*

* cited by examiner

*Primary Examiner* — Brenda L Coleman
*Assistant Examiner* — Madeline E Braun
(74) *Attorney, Agent, or Firm* — ArentFox Schiff LLP; Marlo S. Grolnic

(57) ABSTRACT

The present disclosure relates generally to alkyne containing pharmaceutical agents, and in particular, to phenylethynylthiophene based compounds. More particularly, the present disclosure provides a class of compounds that can inhibit and/or attenuate apoptosis via caspase 3 for the treatment of various degenerative disorders. Additionally, the present disclosure relates to methods for treating specific degenerative disorders such as amyotrophic lateral sclerosis (ALS), Huntington's disease, epilepsy, spinal cord injury, complication due to diabetes, multiple sclerosis (MS), muscular dystrophy (MD), Parkinson's disease (PD), irritable bowel syndrome (IBS) and Alzheimer's disease (AD) in a patient comprising administering to the patient an effective amount of a present compound.

2 Claims, 7 Drawing Sheets

COMPOUNDS AND METHODS FOR THE TREATMENT OF DEGENERATIVE DISORDERS

FIELD

The present disclosure relates generally to alkyne containing compounds that can reduce apoptosis by inhibiting the production of caspase 3.

BACKGROUND

Inflammation is defined as the complex biological response of vascular tissues to harmful stimuli, such as pathogens, damaged cells, or irritants. It is a protective attempt by the organism to remove the injurious stimuli as well as initiate the healing process for the tissue. Inflammation may be acute (early phase of response) or chronic (occurs over a long time). Acute inflammation involves polymorphonuclear neutrophil leukocytes while chronic inflammation involves monocytes, macrophages, lymphocytes and plasma cells (collectively, mononuclear leukocytes). One effect of both acute and chronic inflammation is the degeneration of cells.

Degenerative disorders or diseases cause the death of particular cells (apoptosis). The main human degenerative diseases are divided into three groups: cardiovascular diseases, neoplastic diseases and degenerative diseases of the nervous system (neurodegenerative diseases). Neurodegenerative diseases are caused by the selective death of particular neurons, triggered by characteristic abnormal protein accumulation in the neurons and so on. In some cases of neurodegenerative diseases, genetically defined abnormalities contribute to the development of the disease. The neurodegenerative diseases here include cerebral degenerative disease (e.g., Alzheimer's disease, Parkinson's disease, neuronal damage due to epilepsy, Huntington's disease) and spinal degenerative disease which are a subset of neurodegenerative diseases (e.g., multiple sclerosis, complication due to diabetes, spinal injury, amyotrophic lateral sclerosis). Neuromuscular disease is a subset of neurodegenerative disease that effects the muscles through nerves, motoneurons or neuromuscular junctions (e.g., muscular dystrophy)

Cysteine-aspartic proteases (caspases) are a family of protease enzymes playing essential roles in apoptosis and inflammation. There are currently 12 caspases that have been identified in human cells. Each is synthesized as a catalytically dormant proenzyme. Members of the caspase family can be divided into primarily two main groups based on their substrate specificities: Apoptosis & Pyroptosis.

Apoptosis is programmed cell death that involves the controlled dismantling of intracellular components while avoiding inflammation and damage to surrounding cells. The caspases involved in apoptosis can be subdivided further into two subgroups: Initiator caspases of apoptosis (caspase-2, -8, -9 & -10) and executioner caspases of apoptosis (caspase 3, 6 & 7). Initiator caspases activate executioner caspases that subsequently coordinate their activities to demolish key structural proteins and activate other enzymes. Executioner caspases carry out the mass proteolysis that leads to apoptosis Caspase-3, has been identified as a key executioner of apoptosis in cells. Recent studies in various animals suggest that caspase-3 also functions as a regulatory molecule in neurogenesis and synaptic activity. Knowledge of the biochemical pathway(s) involved in caspase 3 activation and modulation has potential implications for the understanding of synaptic failure in the pathophysiology of various degenerative diseases. Understanding methods for attenuating caspase-3 may offer avenues for treating many neurodegenerative disorders. Pyroptosis is a highly inflammatory form of programmed cell death that occurs most frequently upon infection with intracellular pathogens. Caspases 1, 4 & 5 are primarily involved in pyroptosis.

Amyotrophic lateral sclerosis (ALS) is a neurodegenerative disease with selective loss of motor nerves in the cerebrum, brain stem, and spinal cord that typically affects people of middle or advanced age. ALS causes muscular atrophy and muscular weakness in voluntary muscles in the whole body except for extraocular muscles and eventually causes respiratory failure. People with ALS (PALS) usually die in 3 to 5 years from the onset. Riluzole is the first drug approved for ALS in the US and Japan. Riluzole was originally developed as an anticonvulsant inhibiting glutamate release and has been reported in several clinical trials to exhibit only slight efficacy for the survival of PALS. Edaravone (sold under the name Radicava) is a drug recently approved in the US and while the drug is a known free radical scavenger its mechanism of action in ALS is not entirely understood. In a Phase III trial, Edaravone which is administered via intravenous (i.v.) infusion seemed to slow down the progression of the disease. However, at this time there is no direct clinical evidence indicating that Edaravone is able to extend survival. Thus, there are currently no therapeutic agents effective for ALS under present circumstances. ALS targets motor neurons and neighboring glial cells causing them to gradually break down and die. ALS is inherited in 5 to 10 percent of cases (familial form). The other cases appear to occur randomly (sporadic form). TAR DNA-binding Protein 43 (TDP-43) has been identified as the major pathological protein that is produced in the degenerating motor neurons in sporadic ALS. Of the familial form of ALS, about one-third result from a defect in the gene, C9orf72, the function of which is unknown. Another 20 percent of familial cases result from mutations in the gene that encodes the enzyme copper-zinc superoxide dismutase 1. A specific version of this mutation in mice is the G93A mutant SOD-1 transgenic mouse (SOD1-G93A or SOD-1). In SOD1-G93A mice, microglia have been found to be implicated in ALS initiation. Pasinelli and coworkers (Proc., Natl. Acad. Sci. USA, 97(25), 13901-13906, 2000) have found that the key toxicity events involved with the SOD-1 mutation involve first activation of caspase 1 in the spinal cord followed by caspase 3 activation and then subsequent death of motor neurons. While loss of motor neuron function is the primary symptom in PALS, there are also cognitive effects that are associated with the disease. About 5% of all PALS are clinically diagnosed with frontotemporal dementia (FTD) while another 30-50% exhibit varying levels of executive function impairment. Rosenblum and coworkers (Experimental Neurology, 292, 145-153, (2017)) found that mutating caspase 3 (aspartate to asparagine mutation, D504N) within the excitatory amino acid transporter 2 (EAAT2) in SOD-1-G93A mice delays the development of hind limb and forelimb muscle weakness and increases average lifespan.

Alzheimer's disease (AD) is clinically characterized by progressive amnesia and cognitive impairment, and pathologically by extensive neuronal loss, intraneuronal tangles, and extracellular senile plaques whose cores have a high affinity to Congo red. There are no effective therapies for AD. It has been generally accepted that the clinical manifestation of this disease can be mostly explained by progressive neuronal cell death or apoptosis and that caspase 3 may play a pivotal role (Plociennik et al. Advances in Alzheimer's Disease, 4, 63-77, 2015). For example, D'Amelio and coworkers (Nature Neuroscience, 14, 69-76, 2011), found an enhancement of caspase 3 activity in the Tg2576APPswe mouse model of Alzheimer's disease. They also found that inhibiting caspase 3 activity rescued various observed Alzheimer-like phenotypes.

Huntington's disease (HD) is a neurodegenerative disease whose predominant manifestations consist of chronic progressive involuntary choreiform movements and dementia. Most HD cases are inherited in an autosomal-dominant fashion. Intellectual and psychiatric disorders seen in this disease are originated from extensive atrophy in the cerebral cortex, and pathological changes causing choreiform movements have been thought to be caused by atrophy of the corpus striatum, particularly by that of the caudate nucleus. The HD pathogenesis has been investigated from the standpoint of amine metabolism and extrapyramidal syndrome in brain. A nucleotide sequence encoding polyglutamine on chromosome 4 provides a key to the HD pathogenesis. A glutamine-encoding triplet-nucleotide CAG is normally repeated 10 to 35 times (17 times on average). In HD cases, disease-causative proteins contain polyglutamine regions consisting of 37 or more glutamines. Such abnormal proteins accumulate in neurons and promote apoptosis in which caspases 1 and 3 are involved. Neurons in the corpus striatum are degenerated in HD. They include inhibitory neurons that originally send fibers to the substantia nigra or globus pallidus and release a neurotransmitter gamma-aminobutyric acid (GABA) as well as excitatory neurons that send fibers to the same sites and release a neurotransmitter substance P. In addition, interneurons with short fibers in the corpus striatum, which use acetylcholine as a neurotransmitter, are partially degenerated. The degeneration of dopaminergic neurons projecting fibers from the substantia nigra to the corpus striatum causes the dysfunction of the extrapyramidal system. HD patients usually die of infectious disease or respiratory disorder accompanying dysphagia in 10 to 15 years since the disease onset. Chen and coworkers (Nature Medicine, 6(7), 797-801, 2000) using the R6/2 mouse model of Huntington's disease found that caspase 1 and 3 was upregulated. They also found that when they inhibited their upregulation, they were able to delay disease progression.

Epilepsy is a chronic disease characterized by recurrent convulsions without an apparent cause. These convulsions are transient and occur as a consequence of an excessive or synchronous neuronal activity of the brain. However, by extension, the term "epilepsy" includes a set of diseases characterized by a wide variety of symptoms, an abnormal episodic electrical activity in the brain which causes convulsions being common to all of them. The medicaments currently used for the prevention and/or treatment of epilepsy (antiepileptics) are fundamentally based on (voltage and neuronal receptor-associated) ion channel inhibitor compounds; however, the use of such drugs causes serious side effects in the patients which affect the central nervous system such as ataxia, diplopia (double vision), motor incoordination, hyperactivity, etc., therefore it is necessary to develop new compounds useful for the treatment of epilepsy. Another aspect of epilepsy which no currently approved drug address is the resulting neuronal cell death that accompanies the epileptic seizure. For example, Hershall and coworkers (J. Neurochem. 74, 1215-1223, 2000) found that using a rat model of epileptic seizures they found that caspase 3 protease activity as well as immunoreactivity were both increased in rat brain following seizures.

Parkinson's disease (PD) is a chronic and progressive movement disorder caused by the malfunction and death of neurons in the brain. One aspect of this malfunction is the loss of the neurotransmitter dopamine which is due to the death of dopamine-containing neurons (DPNs) that produce dopamine in the brain. Hartmann and coworkers (Proceedings of the National Academy of Sciences, 97(6), 2875-2880, 2000) have found that both in a 1-methyl-4-phenyl-1,2,3,6-tetrahydropyridine (MPTP)-treated mouse model of Parkinson's disease as well as in postmortem human brain tissues from Parkinson's patients there was a significant increase in activation of caspases 3 in the neurons of both compared to corresponding controls.

Multiple sclerosis (MS) is a disease where the insulating covers of nerve cells in the brain and spinal cord are damaged. In MS, the immune system attacks the protective sheath (myelin) that covers nerve fibers and causes communication problems between the brain and the rest of the body. At later stages of the disease the nerves deteriorate. Meyer and associates (Journal of Neuroscience, 21(16), 6214-6220, 2001) showed that in a rat model of MS, that inflammatory attack of the myelin components lead to neuronal cell death via caspase 3.

Muscular dystrophy (MD) is a group of diseases that make muscles weaker and less flexible over time. There are thirty different kinds of MD and each is different based on the genes that cause it, the muscles it affects, the age when symptoms first appear and how quickly the disease gets worse. For example, Duchenne muscular dystrophy (DMD) is one of the most common MD and affects boys with ages between 3 and 5. Facioscapulohumeral muscular dystrophy (FSHMD) initially affects the skeletal muscles of the face and scapula and upper arms. FSHMD is the third most common form of genetic disease of skeletal muscle. One common similarity among all of the MD diseases is the fact that there are higher levels of apoptosis and caspase 3 among the muscle cells of MD. For example, Sandri and coworkers (Journal of Neuropathology and Experimental Neurology, 60(3), 302-312, 2001) found that in human muscle cells caspase 3 expression, protein and activity level were significantly elevated in both DMD and FSHMD as compared to healthy control tissue.

Spinal cord injury (SCI) can occur due to a sudden blow or cut to the spine. The result of a SCI is permanent changes in strength, sensation and other body functions below the site of injury. SCI can be complete or incomplete. With a complete SCI, the cord can't send signals below the level of the injury. As a result, the person is paralyzed below the injury. With an incomplete injury, the person has some movement and sensation below the injury. McEwen and coworkers (Journal of Histochemistry & Cytochemistry, 53(7), 809-819, 2005), have demonstrated that in a rat model of SCI, biochemical changes occur after spinal injury that lead to apoptotic cell death via caspase 3. McEwen and coworkers also found a biphasic pattern of caspase-3 activation during the first 8 days post-injury, suggesting that at least two mechanisms activate caspase-3 following SCI. Evelyne & Coworkers (Neurosurg. Focus, 6(1), Article 7, 1999) showed that in human spinal cords from postmortem patients who died after traumatic SCI, there was an elevation of caspase 3 within the cells in and around the spinal cord of 14 of the 15 spinal cords examined.

Diabetes is a disease in which the body's ability to produce or respond to insulin is impaired resulting in abnormal metabolism of carbohydrates and elevated blood glucose level. Beta cells are located in the pancreas and are responsible for producing insulin. Cnop and coworkers (Diabetes, 54(supplement 2), S97-S107, 2005) found that one key mechanism for beta cells death is through the activation of interleukin 1-beta that then activates caspase 3. One aspect to the abnormal metabolism is the level diabetes induced cellular damage (DICD) in the brain and spinal cord among experimental and clinical stroke subjects with diabetes. Muranyi and coworkers (diabetes, 52, 481-486, 2003) showed that in the streptozotocin (STZ) rat model of diabetes there was an enhanced level of apoptosis via caspase 3 in STZ rodents subjected to cerebral ischemia as compared to normal controls. This enhanced level of apoptosis has been found to occur in both the brain and spin and some scientist have linked Type 2 diabetes with Alzheimer's disease (de La Monte, and coworkers, Journal of Diabetes Science and Technology, 2(6), 1101-1113 (2008)).

Inflammatory bowel disease (IBD) comprises primarily 2 disorders: Ulcerative colitis (UC) and Crohn's disease (CD). The hallmark of IBD is chronic, uncontrolled inflammation of the intestinal mucosa, which can affect any part of the gastrointestinal tract. In healthy people, the intestine becomes inflamed in response to a potential pathogen, then returns to a state of tolerance once the pathogen is eradicated from the gut. In individuals with IBD, however, inflammation is not down-regulated, the mucosal immune system remains chronically activated, and the intestine remains chronically inflamed. Genome-wide association studies performed in geographically distant populations have identified single nucleotide polymorphisms (SNP) in various genes as strongly associated variants in Crohn's disease. Murphy and coworkers (Nature, 506, 456-462, (2014) found that a SNP in one of these genes causes enhanced caspase 3 activation leading to accelerated degradation and apoptosis resulting to a predisposition toward Crohn's disease. Most recently, Quigley (Quigley, E. M. M., Journal of Clinical Medicine, volume 7(6), pages 1-8, (2018)) discusses the relation between IBD and the central nervous system termed the "gut-brain axis" whereby components of the gut microbiota can influence brain morphology and function including behavior and cognition. Main and Minter (Frontiers in Neuroscience, Volume 11, article 151, pages 1-8 (2017) have also recently focused attention on the microbiota or the microbiome and its impact in neuroinflammation and neurodegenerative diseases.

Matrix metalloproteinases (MMPs) are a family of structurally related zinc-containing enzymes that have been reported to mediate the breakdown of connective tissue in normal physiological processes such as embryonic development, reproduction, and tissue remodelling. MMP-2 (72 kDa gelatinase/Gelatinase A) and MMP-9 (92 kDa gelatinase/Gelatinase B) degrade the extra cellular matrix components of the basement membrane. Their substrates include types IV and V collagen, fibronectin, elastin, and denatured interstitial collagens. Matrix degradation attributed to this proteinase has been shown to play an important role in the progression of such diseases as arteriosclerosis, tumor growth and metastasis. Sucholeiki (WO/2010/075287) has shown that partially deuterating a dual active MMP-2 and MMP-9 inhibitor can enhance the bioavailability of that inhibitor (i.e., Compound 118) as compared its non-deuterated parent (i.e., Compound 5). Sucholeiki (WO/2010/075287) also has shown that most MMP inhibitors contain a hydroxamic acid that can produce various toxicities such as muscular skeletal syndrome. Kesanakurti and coworkers (PloS ONE, 6(5), e-19341, 1-14, 2011), have demonstrated that within glioblastomas (GBM) cells which are a form of brain tumor that upon downregulation of MMP-2 there is a significant activation of caspase 8 and caspase 3 and a hike in apoptotic cell death. Chetty and coworkers (Mol. Cancer Ther., 9(9), 2605-2617, 2010) found similarly that in human glioblastoma cell lines that MMP-9 inhibition induced apoptosis via caspase 8 & 3 activation. Nyomoi and coworkers (Cell Death and Differentiation, 10, 558-559, 2003), treated breast, melanoma, leukemia, osteosarcoma, and normal breast epithelial cells with (2R)-2-[(4-biphenylsulfonyl) amino]-3-phenylproprionic acid a known inhibitor of MMP-2 and MMP-9 to induce apoptosis. From these examples it is clear that inhibition of MMP-2 and/or MMP-9 though their down regulation or via their direct inhibition upset and/or disrupt the processes of certain cells. When theses cell processes are disrupted it triggers an elevation of various caspases resulting in apoptosis or cell death.

The present disclosure relates to the use of alkyne containing small molecule compounds that can be used to treat neurodegenerative disorders such as ALS, Huntington's disease, epilepsy, spinal injury, complication due to diabetes, MS, MD, PD, IBS and Alzheimer's disease by reducing and/or attenuating caspase 3 protein levels within cells resulting in a reduction in apoptosis. These alkyne containing small molecule compounds exhibit good chemical stability, oral bioavailability in plasma and target tissue penetration in the spine and brain.

SUMMARY

The present disclosure relates to a class of alkyne containing pharmaceutical agents and its method of use in the treatment of various neurodegenerative disorders.

The present disclosure provides a class of alkyne inhibiting compounds that are represented by the general Formula (I):

(I)

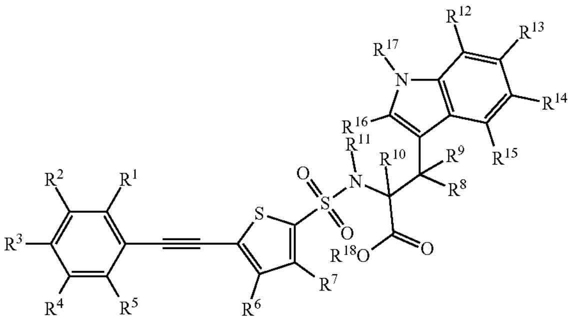

wherein all variables in the preceding Formulas (I) are as defined herein below.

$R^1$, $R^2$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ is independently selected from the group consisting of deuterium, hydrogen, alkyl, deuteroalkyl:

$R^3$ is independently selected from the group consisting of $CD_3$ and $CH_3$;

$R^{18}$ is independently selected from the group consisting of hydrogen, deuterium, alkyl, deuteroalkyl, alkylammonium, sodium, potassium, calcium, zinc, meglumine;

N-oxides, pharmaceutically acceptable salts, and stereoisomers thereof.

The compounds of the present disclosure may be used in the treatment of neurodegenerative disorders involving the death of neurons via apoptosis, such as ALS, Huntington's disease, epilepsy, spinal injury, complication due to diabetes, MS, MD, PD, IBS and Alzheimer's disease by reducing the levels of caspase 3.

In particular the alkyne containing compounds of the present disclosure may be used in the treatment of loss of motor or neuronal activity in a patient, said method comprising the step of administering to the patient an effective amount of a present compound in combination with a carrier, wherein the patient is suffering from loss of motor and/or neuronal activity from ALS, Huntington's disease, epilepsy, spinal injury, complication due to diabetes, MS, MD, PD, IBS and AD.

The present disclosure also contemplates use of such compounds in pharmaceutical compositions for oral or parenteral administration, comprising one or more of the alkyne containing compounds disclosed herein.

The present disclosure further provides methods of inhibiting and/or attenuating apoptosis by reducing caspase 3 protein levels, by administering formulations, including, but not limited to, oral, rectal, topical, intravenous, parenteral (including, but not limited to, intramuscular, intravenous), intrathecal, intraspinal, epidural, ocular (ophthalmic), transdermal, inhalative (including, but not limited to, pulmonary, aerosol inhalation), nasal, sublingual, subcutaneous or intraarticular formulations, comprising the alkyne containing compounds by standard methods known in medical practice, for the treatment of disorders or symptoms arising from or upregulation of caspase 3 leading to apoptosis. Although the most suitable route in any given case will depend on the nature and severity of the conditions being treated and on the nature of the active ingredient. The compounds from this disclosure are conveniently presented in unit dosage form and prepared by any of the methods well known in the art of pharmacy.

The alkyne containing compounds of the present disclosure may be used in combination with a disease modifying antirheumatic drug, a nonsteroidal anti-inflammatory drug, a COX-2 selective inhibitor, a COX-1 inhibitor, an immunosuppressive, a steroid, a biological response modifier or other anti-inflammatory agents.

BRIEF DESCRIPTION OF THE DRAWINGS

The disclosure will be more fully understood by reference to the detailed description, in conjunction with the following figures, wherein.

DETAILED DESCRIPTION

Figure 1:
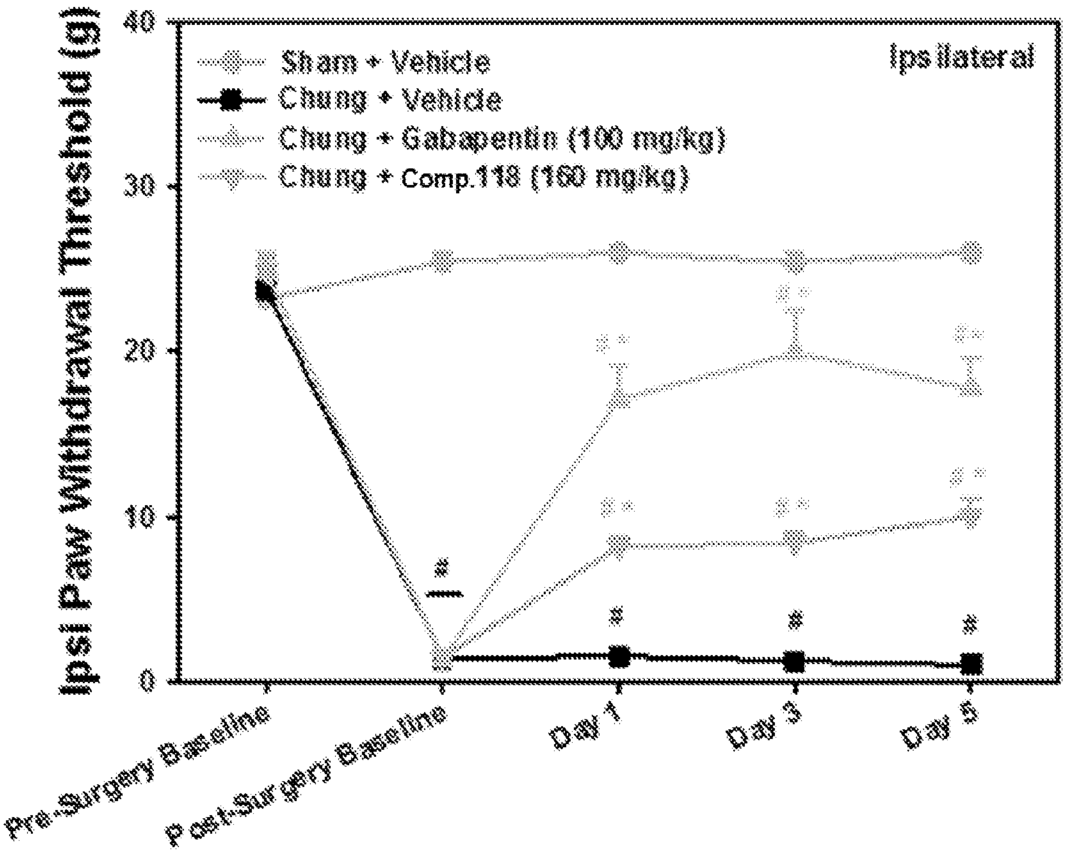
FIG. 1 is a graph representing mechanical allodynia as measured via paw withdrawal threshold at different time points before and after spinal nerve ligation (SNL) surgery as per the Chung Model.

The term "D" as used herein alone or as part of a chemical structure or group, denotes deuterium.

The term "deutero" as used herein alone or as part of a group, denote optionally substituted deuterium atoms.

Neurons or nerve cells are the fundamental building block of the brain and central nervous system (i.e. spinal cord), the cells responsible for receiving sensory input from the external world, for sending motor commands to our muscles, and for transforming and relaying the electrical signals at every step in between. Neurons normally do not reproduce or replace themselves, so when they become damaged or die they cannot be replaced by the body.

The term "neurodegenerative diseases" is an umbrella term for a range of conditions which primarily affect the neurons. Examples of neurodegenerative diseases include ALS, Huntington's disease, MS, muscular dystrophy MD, PD, IBS and AD. Neurodegenerative diseases are incurable and debilitating conditions that result in progressive degeneration and/or death of neurons or nerve cells.

The term "glial cells" as used herein denotes a type of cell that surrounds neurons and provide support for and insulation between them. Glial cells are the most abundant cell types in the central nervous system. Glial cells are non-neuronal cells in the central nervous system (brain and spinal cord) and the peripheral nervous system that do not produce electrical impulses. They maintain homeostasis, form myelin, and provide support and protection for neurons. In the central nervous system, glial cells include oligodendrocytes, astrocytes, ependymal cells, and microglia, and in the peripheral nervous system glial cells include Schwann cells and satellite cells.

The term "apoptosis" as used herein is a form of cell death that is generally triggered by normal, processes in the body. For the apoptotic pathways that cause cell death, the primary molecular signals are inactive proenzymes called caspases.

The term "necrosis" as used herein is a form of cell death that is triggered by external factors or diseases, such as trauma or infection. Necrosis sometimes makes uses of caspases, but to a much lesser degree than in the apoptotic pathway.

The terms "alkyl" as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: deuterium, halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl The terms "lower alk" or "lower alkyl" as used herein, denote such optionally substituted groups as described above for alkyl having 1 to 4 carbon atoms in the normal chain.

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include, but are not limited to, ethynyl, propynyl, butynyl, pentynyl, hexynyl, heptynyl, octynyl, nonynyl, decynyl, and the like. Exemplary substituents may include, but are not limited to, one or more of the following groups: deutero, halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include, but are not limited to, phenyl, biphenyl, and naphthyl. Exemplary substituents include, but are not limited to, one or more nitro groups, alkyl groups as described above or groups described above as alkyl substituents.

The term "heterocycle" or "heterocyclic system" denotes a heterocyclyl, heterocyclenyl, or heteroaryl group as described herein, which contains carbon atoms and from 1 to 4 heteroatoms independently selected from N, O and S and including any bicyclic or tricyclic group in which any of the above-defined heterocyclic rings is fused to one or more heterocycle, aryl or cycloalkyl groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom.

Examples of heterocycles include, but are not limited to 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolinyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl.

"Heterocyclenyl" denotes a non-aromatic monocyclic or multicyclic hydrocarbon ring system of about 3 to about 10 atoms, desirably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Ring sizes of rings of the ring system may include 5 to 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more substituents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960), the contents all of which are incorporated by reference herein. Exemplary monocyclic azaheterocyclenyl groups include, but are not limited to, 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include, but are not limited to, 3,4-dihydro-2H-pyran, dihydrofuranyl, and fluorodihydrofuranyl. An exemplary multicyclic oxaheterocyclenyl group is 7-oxabicyclo [2.2.1]heptenyl.

"Heterocyclyl," or "heterocycloalkyl," denotes a non-aromatic saturated monocyclic or multicyclic ring system of about 3 to about 10 carbon atoms, desirably 4 to 8 carbon atoms, in which one or more of the carbon atoms in the ring system is/are hetero element(s) other than carbon, for example nitrogen, oxygen or sulfur. Ring sizes of rings of the ring system may include 5 to 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" denotes an aromatic monocyclic or multicyclic ring system of about 5 to about 10 atoms, in which one or more of the atoms in the ring system is/are hetero element(s) other than carbon, for example nitrogen, oxygen or sulfur. Ring sizes of rings of the ring system include 5 to 6 ring atoms. The "heteroaryl" may also be substituted by one or more substituents which may be the same or different, and are as defined herein. The designation of the aza, oxa or thia as a prefix before heteroaryl define that at least a nitrogen, oxygen or sulfur atom is present respectively as a ring atom. A nitrogen atom of a heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include, but are not limited to, pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,3-triazinyl, 1,2,4-triazinyl, 1,3,5-triazinyl, benzthiazolyl, dioxolyl, furanyl, imidazolyl, indolyl, indolizinyl, isoxazolyl, isoquinolinyl, isothiazolyl, oxadiazolyl, oxazinyl, oxiranyl, piperazinyl, piperidinyl, pyranyl, pyrazinyl, pyridazinyl, pyrazolyl, pyridyl, pyrimidinyl, pyrrolyl, pyrrolidinyl, quinazolinyl, quinolinyl, tetrazinyl, tetrazolyl, 1,3,4-thiadiazolyl, 1,2,3-thiadiazolyl, 1,2,4-thiadiazolyl, 1,2,5-thiadiazolyl, thiatriazolyl, thiazinyl, thiazolyl, thienyl, 5-thioxo-1,2,4-diazolyl, thiomorpholino, thiophenyl, thiopyranyl, triazolyl and triazolonyl.

The terms "halogen", "halo", or "hal", as used herein alone or as part of another group, denote chlorine, bromine, fluorine, and iodine.

The term "haloalkyl" denotes a halo group as described above bonded though an alkyl, as defined above. Fluoroalkyl is an exemplary group.

The term "deuteroalkyl" denotes a deutero group as described above bonded through an alkyl, as defined above. Trideuteromethane is an exemplary group.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, non-aqueous media like ethers, ethyl acetate, ethanol, isopropanol, or acetonitrile. Lists of suitable salts are found in Remington's Pharmaceutical Sciences, 18th ed., Mack Publishing Company, Easton, PA, 1990, p. 1445, the disclosure of which is hereby incorporated by reference.

Paulekuhn and coworkers (J. Med. Chem. 50, 6665-6672, (2007)) analyzed the Orange Book database published by the U.S. Drug and Food Administration (FDA) to determine what the frequency of occurrences of different counterions used for formation of pharmaceuticals salts. They found that among the cations used to form oral dosage forms of active pharmaceutical ingredients salts of acidic molecules, the sodium ion strongly dominated (~65%). The second largest was potassium (~13%) followed by calcium (~12%), magnesium (~3%), tromethamine (~3%) with piperazine (~1%), cholinate (~1%) and benzathine (~1%) all tied for last. Among counterions used for injectable formulations, sodium was the highest (~85%) followed by meglumine (~5%) and calcium (~3%). The remaining cations that each comprised ~1% were benzathine, diethanolamine, diethylamine, lysine, potassium, procaine and tromethamine. The compound salts of the present disclosure include, but are not limited to, all of the above listed counterions formulated for either oral use or as an injectable.

The term "isotopic enrichment" refers to a process by which the relative abundance of an isotope of a given element are altered, thus producing a form of the element that has been enriched in one particular isotope and depleted in its other isotopic forms. Thus, the disclosure encompasses all percent levels of isotopic enrichment of compounds of Formulas (I). Exemplary percent levels of isotopic enrichment for deuterium include, but are not limited to, >97%, >95%, >85%, >50%, >30%, >20%, >5% & >1%.

The term "effective amount" refers to an amount sufficient to produce the desired effect, e.g., to reduce or ameliorate the severity, duration, progression, or onset of a disease, condition, or disorder (e.g., a disease, condition, or disorder related to loss of neuronal cells or cell function), or one or more symptoms thereof; prevent the advancement of a disease, condition, or disorder; cause the regression of a disease, condition, or disorder; prevent the recurrence, development, onset or progression of a symptom associated with a disease, condition, or disorder; or enhance or improve the prophylactic or therapeutic effect(s) of another therapy. An effective amount of a compound according to this disclosure can range from, e.g., about 0.001 mg/kg to about 1000 mg/kg, or in certain embodiments, about 0.01 mg/kg to about 100 mg/kg, or in certain embodiments, about 0.1 mg/kg to about 50 mg/kg. Effective doses will also vary, as recognized by those skilled in the art, depending on the disorder treated, route of administration, excipient usage, the age and sex of the subject, and the possibility of co-usage with other therapeutic treatments such as use of other agents.

The term "racemic mixture" denotes a mixture that is about 50% of one enantiomer and about 50% of the corresponding enantiomer relative to all chiral centers in the molecule. Thus, the disclosure encompasses all enantiomerically-pure, enantiomerically-enriched, and racemic mixtures of compounds of Formulas (I).

The phrase "pharmaceutically acceptable" denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "N-oxide" denotes compounds that can be obtained in a known manner by reacting a compound of the present disclosure including a nitrogen atom (such as in a pyridyl group) with hydrogen peroxide or a peracid, such as 3-chloroperoxy-benzoic acid, in an inert solvent, such as dichloromethane, at a temperature between about −10-80° C., desirably about 0° C.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Unless moieties of a compound of the present disclosure are defined as being unsubstituted, the moieties of the compound may be substituted. In addition to any substituents provided above, the moieties of the compounds of the present disclosure may be optionally substituted with one or more groups independently selected from:

$C_1$-$C_4$ alkyl;
$C_2$-$C_4$ alkenyl;
$C_2$-$C_4$ alkynyl;
$CF_3$;
halo;
OH;
O—($C_1$-$C_4$ alkyl);
$OCH_2F$;
$OCHF_2$;
$OCF_3$;
OC(O)—($C_1$-$C_4$ alkyl);
OC(O)—($C_1$-$C_4$ alkyl);
OC(O)NH—($C_1$-$C_4$ alkyl);
OC(O)N($C_1$-$C_4$ alkyl)$_2$;
OC(S)NH—($C_1$-$C_4$ alkyl);
OC(S)N($C_1$-$C_4$ alkyl)$_2$;
SH;
S—($C_1$-$C_4$ alkyl);
S(O)—($C_1$-$C_4$ alkyl);
S(O)$_2$—($C_1$-$C_4$ alkyl);
SC(O)—($C_1$-$C_4$ alkyl);
SC(O)O—($C_1$-$C_4$ alkyl);
$NH_2$;
N(H)—($C_1$-$C_4$ alkyl);
N($C_1$-$C_4$ alkyl)$_2$;
N(H)C(O)—($C_1$-$C_4$ alkyl);
N($CH_3$)C(O)—($C_1$-$C_4$ alkyl);
N(H)C(O)—$CF_3$;
N($CH_3$)C(O)—$CF_3$;
N(H)C(S)—($C_1$-$C_4$ alkyl);
N($CH_3$)C(S)—($C_1$-$C_4$ alkyl);
N(H)S(O)$_2$—($C_1$-$C_4$ alkyl);
N(H)C(O)$NH_2$;
N(H)C(O)NH—($C_1$-$C_4$ alkyl);
N($CH_3$)C(O)NH—($C_1$-$C_4$ alkyl);
N(H)C(O)N($C_1$-$C_4$ alkyl)$_2$;
N($CH_3$)C(O)N($C_1$-$C_4$ alkyl)$_2$;
N(H)S(O)$_2$$NH_2$);
N(H)S(O)$_2$NH—($C_1$-$C_4$ alkyl);
N($CH_3$)S(O)$_2$NH—($C_1$-$C_4$ alkyl);
N(H)S(O)$_2$N($C_1$-$C_4$ alkyl)$_2$;
N($CH_3$)S(O)$_2$N($C_1$-$C_4$ alkyl)$_2$;
N(H)C(O)O—($C_1$-$C_4$ alkyl);
N($CH_3$)C(O)O—($C_1$-$C_4$ alkyl);
N(H)S(O)$_2$O—($C_1$-$C_4$ alkyl);
N($CH_3$)S(O)$_2$O—($C_1$-$C_4$ alkyl);
N($CH_3$)C(S)NH—($C_1$-$C_4$ alkyl);
N($CH_3$)C(S)N($C_1$-$C_4$ alkyl)$_2$;
N($CH_3$)C(S)O—($C_1$-$C_4$ alkyl);
N(H)C(S)$NH_2$;
$NO_2$;
$CO_2H$;
$CO_2$—($C_1$-$C_4$ alkyl);
C(O)N(H)OH;
C(O)N($CH_3$)OH:
C(O)N($CH_3$)OH;
C(O)N($CH_3$)O—($C_1$-$C_4$ alkyl);
C(O)N(H)—($C_1$-$C_4$ alkyl);
C(O)N($C_1$-$C_4$ alkyl)$_2$;
C(S)N(H)—($C_1$-$C_4$ alkyl);
C(S)N($C_1$-$C_4$ alkyl)$_2$;
C(NH)N(H)—($C_1$-$C_4$ alkyl);
C(NH)N($C_1$-$C_4$ alkyl)$_2$;
C($NCH_3$)N(H)—($C_1$-$C_4$ alkyl);
C($NCH_3$)N($C_1$-$C_4$ alkyl)$_2$;
C(O)—($C_1$-$C_4$ alkyl);
C(NH)—($C_1$-$C_4$ alkyl);
C($NCH_3$)—($C_1$-$C_4$ alkyl);
C(NOH)—($C_1$-$C_4$ alkyl);
C($NOCH_3$)—($C_1$-$C_4$ alkyl);
CN;
CHO;
$CH_2OH$;
$CH_2O$—($C_1$-$C_4$ alkyl);
$CH_2NH_2$;
$CH_2N$(H)—($C_1$-$C_4$ alkyl);
$CH_2N$($C_1$-$C_4$ alkyl)$_2$;
aryl;
heteroaryl;
cycloalkyl; and
heterocyclyl.

In one embodiment of the present disclosure, the alkyne containing metalloprotease inhibiting compounds may be represented by the general Formula (I):

(I)

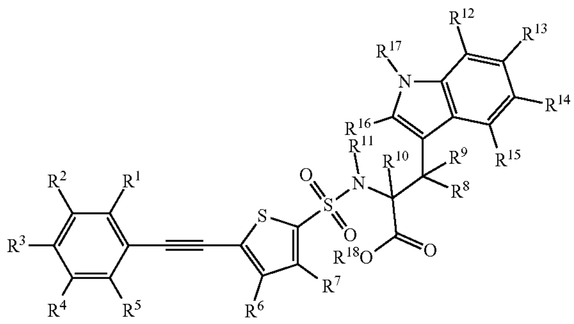

wherein all variables in the preceding Formulas (I) are as defined herein below.

$R^1$, $R^2$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ is independently selected from the group consisting of deuterium, hydrogen, methyl, deuteromethyl alkyl, deuteroalkyl;

$R^3$ is independently selected from the group consisting of $CD_3$ and $CH_3$;

$R^{18}$ is independently selected from the group consisting of hydrogen, deuterium, alkyl, deuteroalkyl, alkylammonium, sodium, potassium, calcium, zinc, meglumine;

N-oxides, prodrugs, pharmaceutically acceptable salts, and stereoisomers thereof.

It is contemplated that the compounds of the present disclosure represented by the Formula described above include all diastereomers and enantiomers, as well as racemic mixtures. Racemic mixtures may be separated by chiral salt resolution or by chiral column HPLC chromatography.

More specifically, the compounds of Formula (I) may be selected from, but are not limited to, the following:
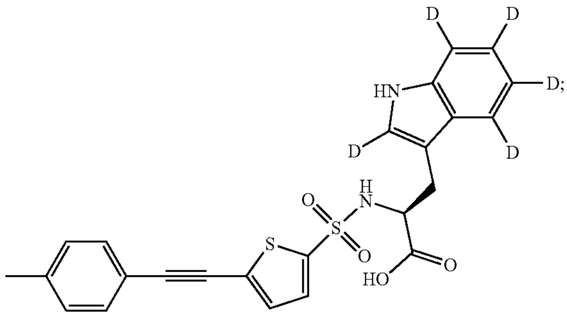
82
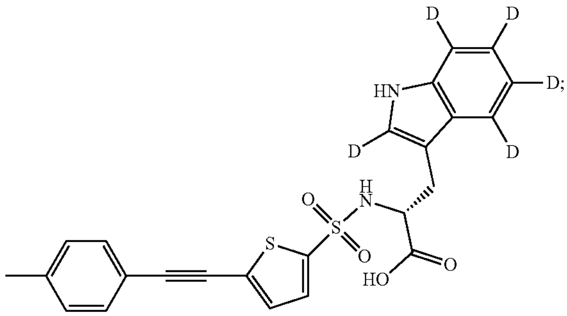
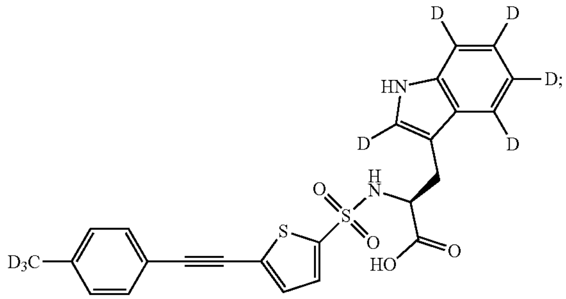
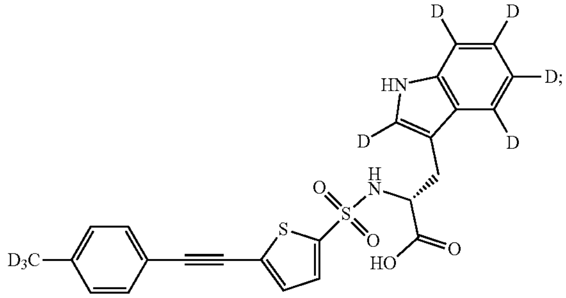
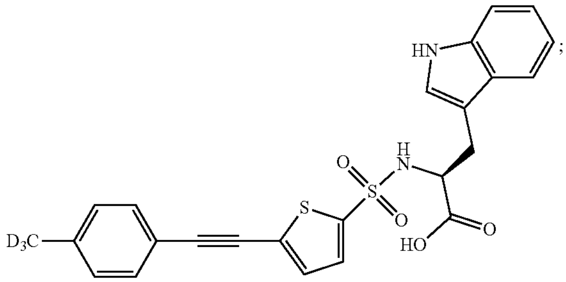
-continued
118
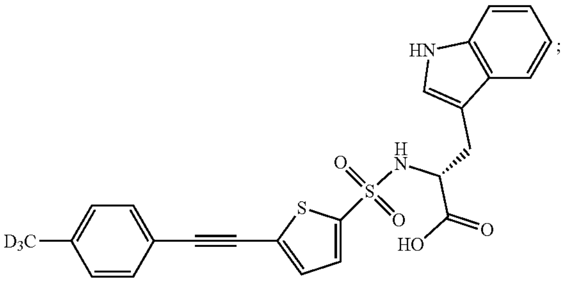
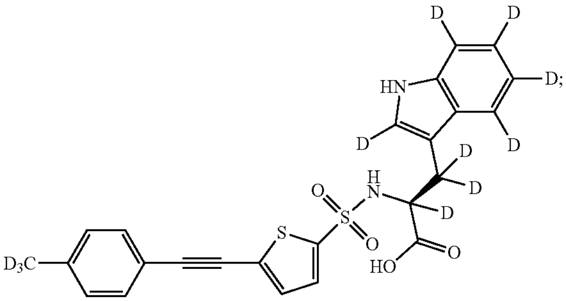
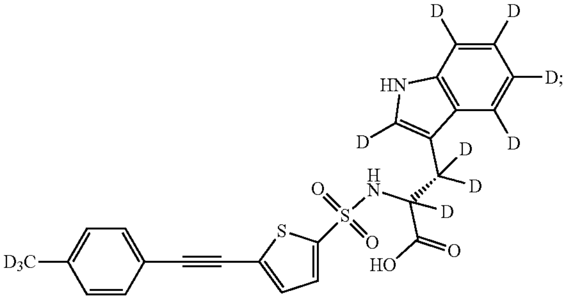
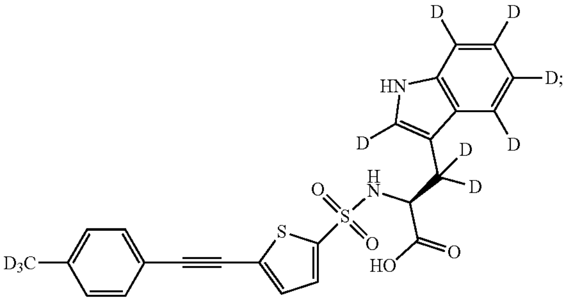
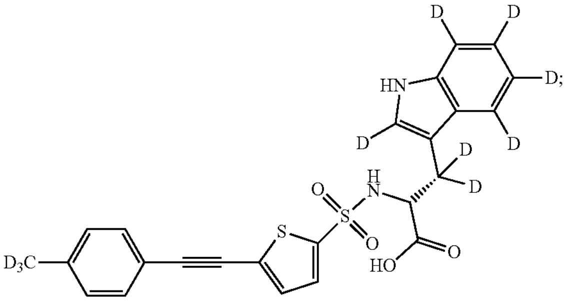

-continued
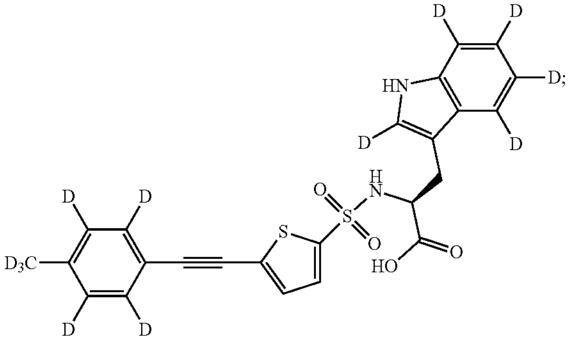
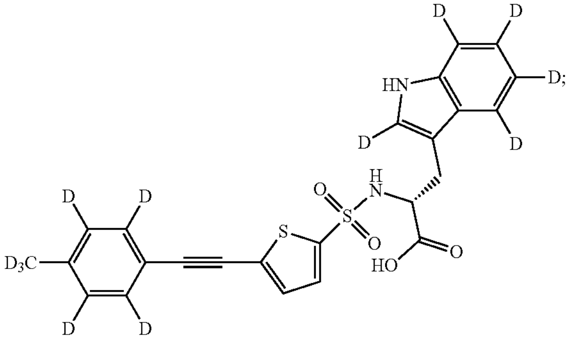
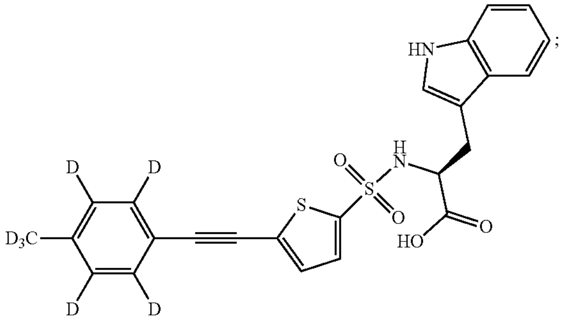
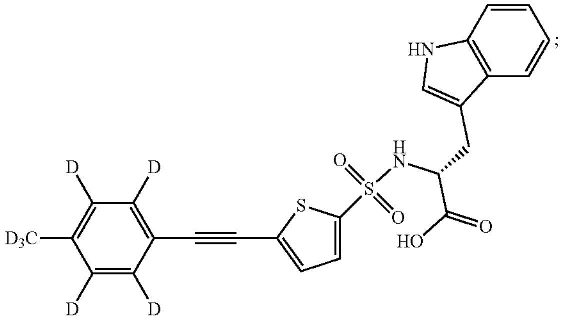
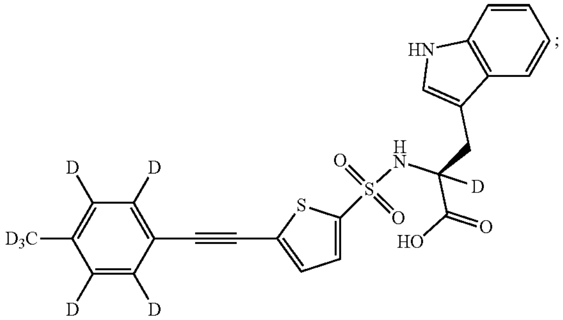
-continued
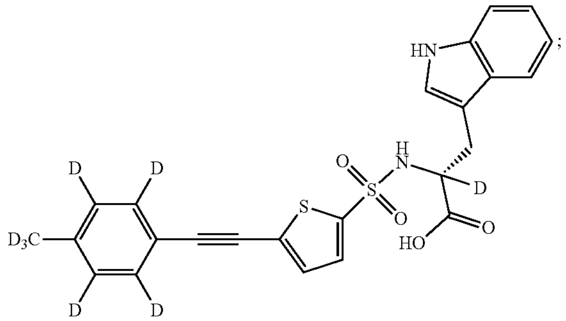
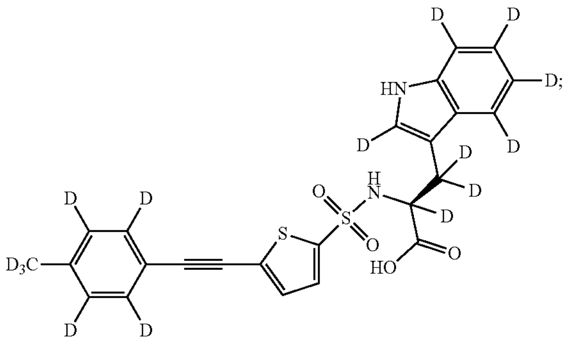
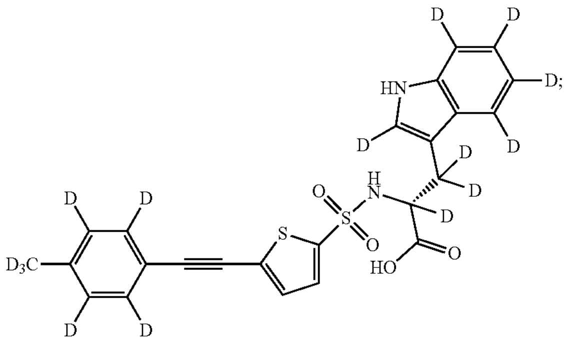
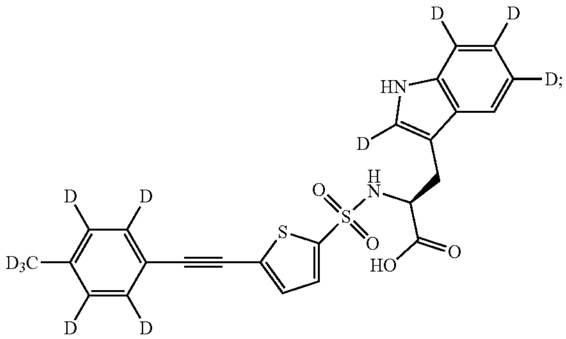
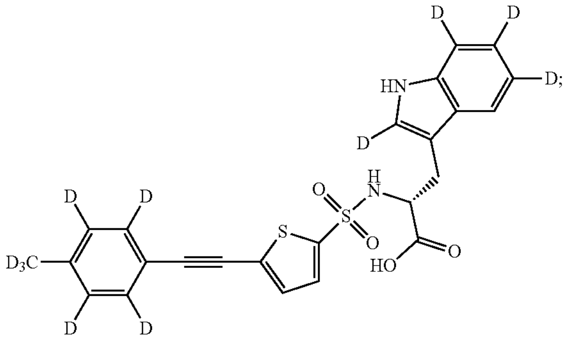

-continued
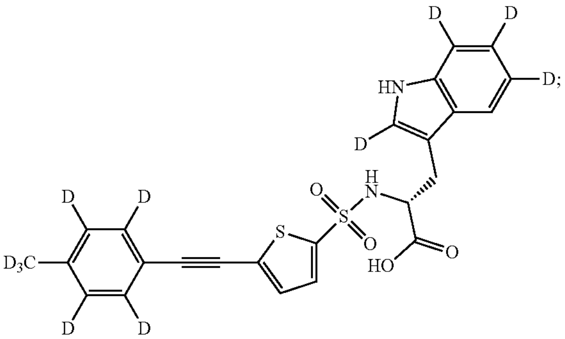
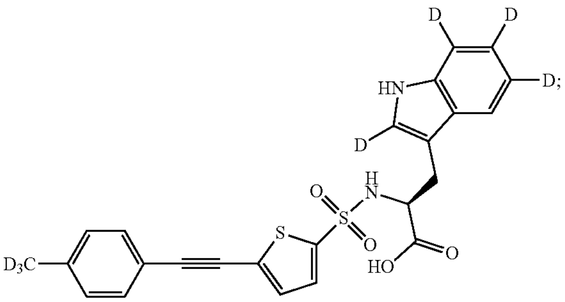
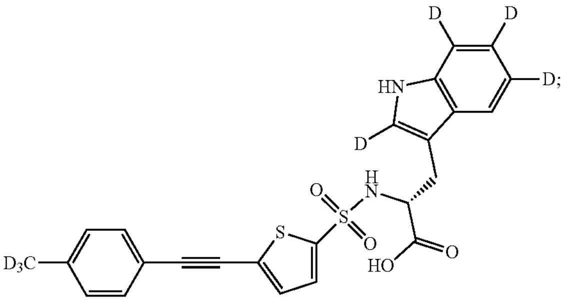
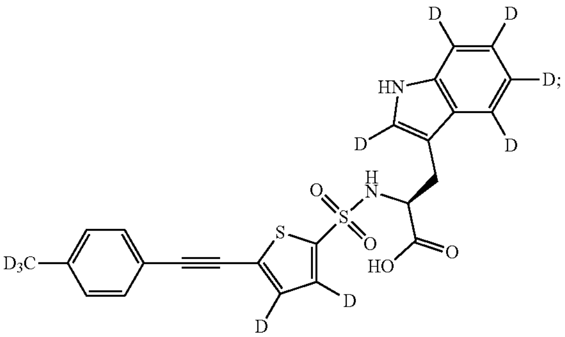
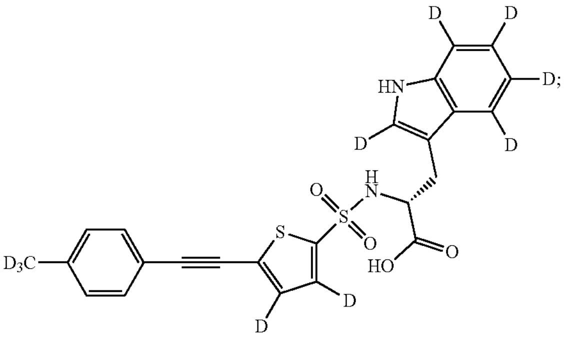
-continued
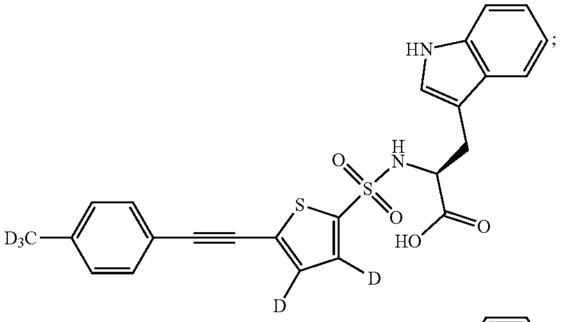
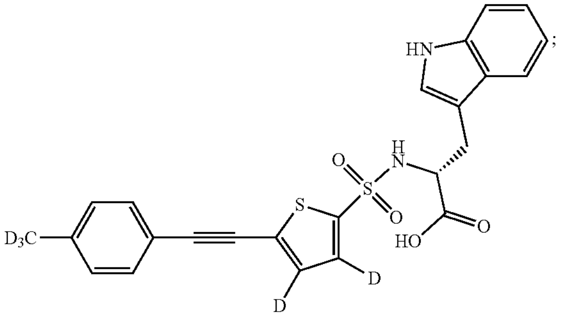
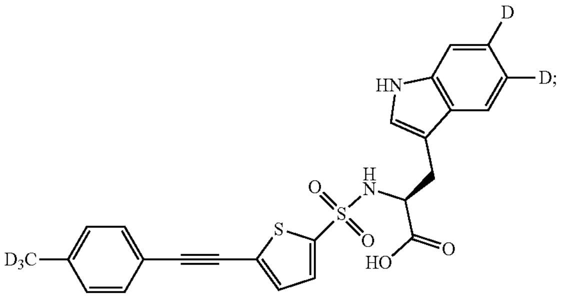
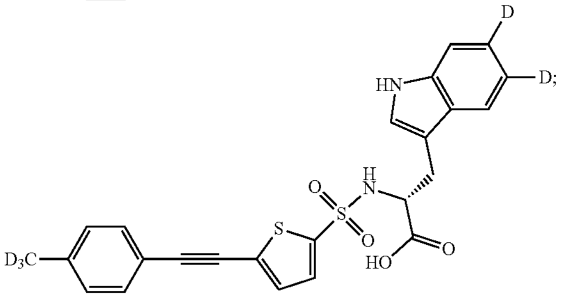
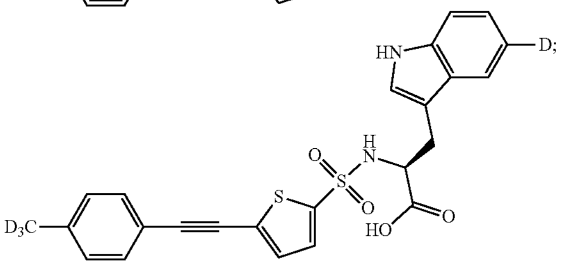
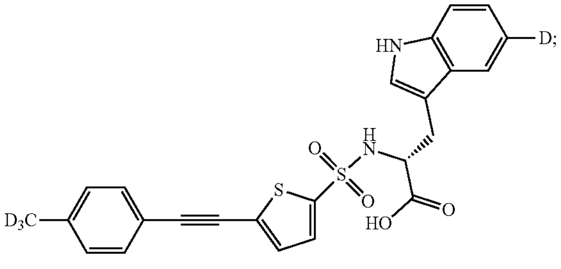

-continued
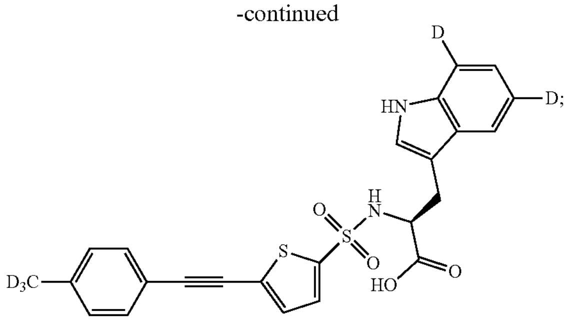
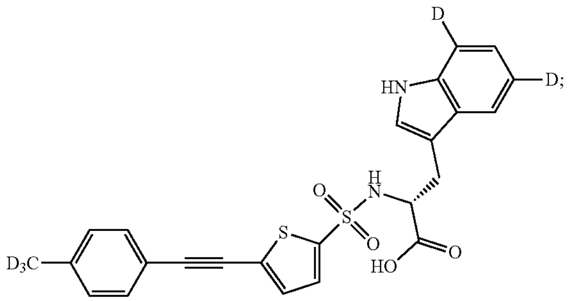
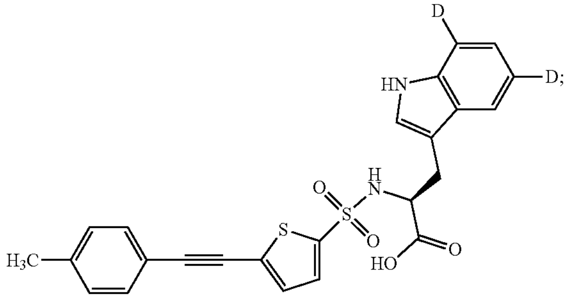
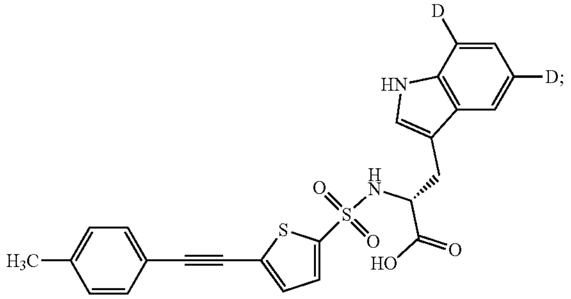
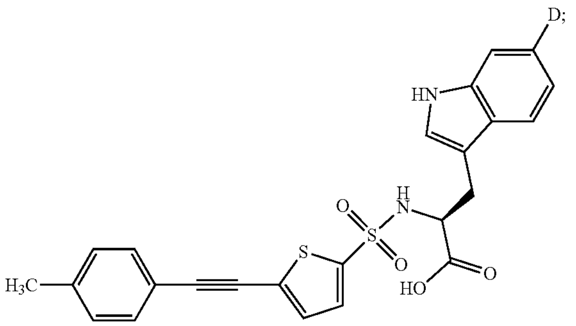
-continued
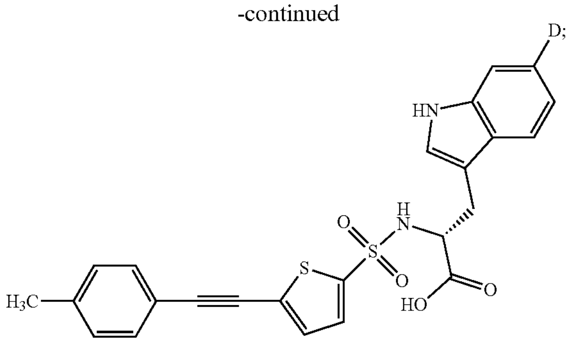
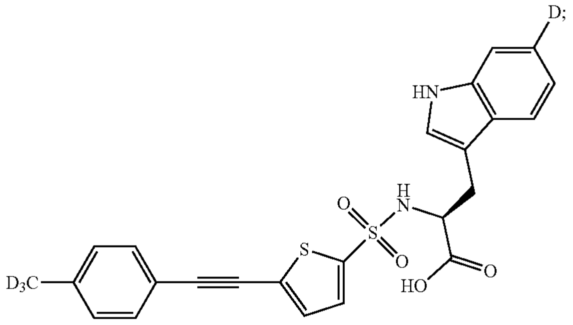
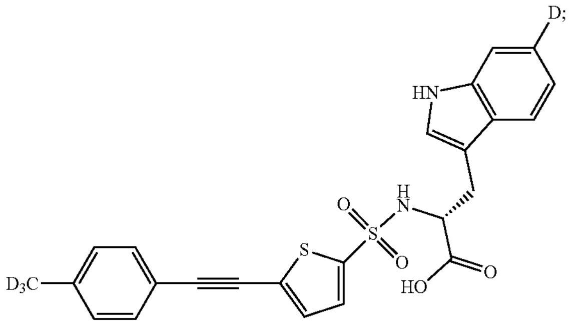
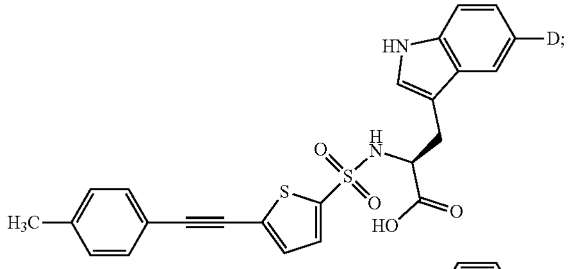
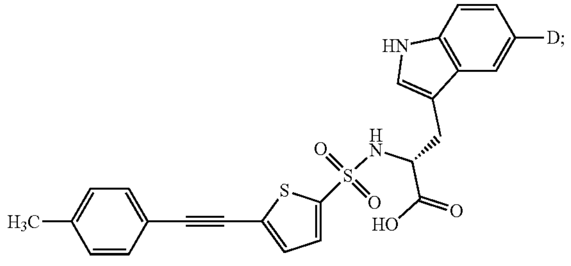

-continued

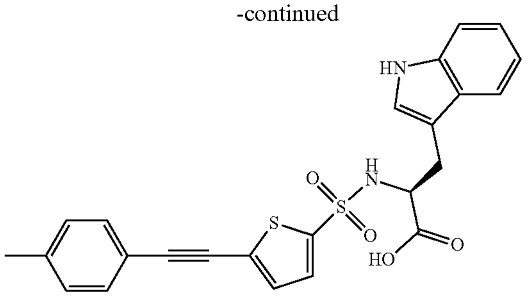

and

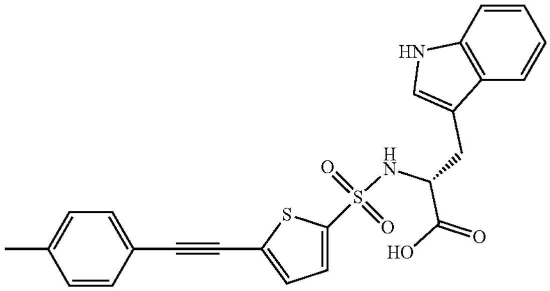

;

The present disclosure also is directed to pharmaceutical compositions including any of the apoptosis attenuating compounds of the present disclosure described above. In accordance therewith, some embodiments of the present disclosure provide a pharmaceutical composition which may include an effective amount of an alkyne containing compound of the present disclosure and a pharmaceutically acceptable carrier.

In some embodiments of the present disclosure, the alkyne containing compounds defined above are used in the manufacture of a medicament for the treatment of neurodegenerative disorders or diseases. The alkyne containing compounds defined above may be used in combination with a drug, agent or therapeutic such as, but not limited to: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; or (h) other anti-inflammatory agents or therapeutics useful for the treatment of chemokine mediated diseases.

Examples of disease modifying antirheumatic drugs include, but are not limited to, methotrexate, azathioptrineluflunomide, penicillamine, gold salts, mycophenolate, mofetil and cyclophosphamide.

Examples of nonsteroidal anti-inflammatory drugs include, but are not limited to, piroxicam, ketoprofen, naproxen, indomethacin, and ibuprofen.

Examples of COX-2 selective inhibitors include, but are not limited to, rofecoxib, celecoxib, and valdecoxib.

An example of a COX-1 inhibitor includes, but is not limited to, piroxicam.

Examples of immunosuppressive include, but are not limited to, methotrexate, cyclosporin, leflunimide, tacrolimus, rapamycin and sulfasalazine.

Examples of steroids include, but are not limited to, p-methasone, prednisone, cortisone, prednisolone and dexamethasone.

Examples of biological response modifiers include, but are not limited to, anti-TNF antibodies, TNF-α antagonists, IL-1 antagonists, anti-CD40, anti-CD28, IL-10 and anti-adhesion molecules.

Examples of anti-inflammatory agents or therapeutics include, but are not limited to, p38 kinase inhibitors, PDE4 inhibitors, TACE inhibitors, chemokine receptor antagonists, thalidomide, leukotriene inhibitors and other small molecule inhibitors of pro-inflammatory cytokine production.

In accordance with another embodiment of the present disclosure, a pharmaceutical composition may include an effective amount of a compound of the present disclosure, a pharmaceutically acceptable carrier and a drug, agent or therapeutic selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; or (h) other anti-inflammatory agents or therapeutics useful for the treatment of chemokine mediated diseases.

The level of caspase 3 which is reduced through the action of the alkyne containing compounds of the present disclosure may be measured using any suitable assay known in the art. Standard in vitro tests for measuring caspase 3 expression, enzyme activity and protein level are described in Examples 10-14. The in vivo antidegenerative properties of the compounds of the present disclosure may be measured using any suitable animal models of degenerative disease known in the art. Standard in vivo tests for measuring the level of ambulatory, sensory, biochemical and/or cellular activity are described in separate animal models described in Examples 17, 18, 20-24.

The synthesis and pharmacokinetics (PK) of antidegenerative compounds of the present disclosure and their biological assays are described in the following examples which are not intended to be limiting in any way.

EXAMPLES AND METHODS

Example 1

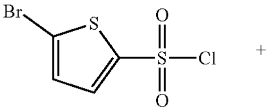

1

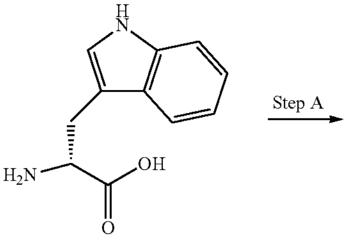

2

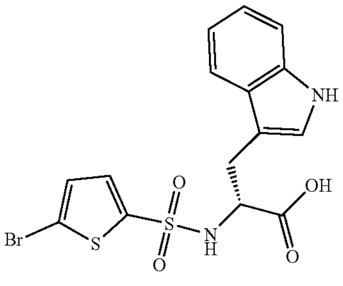

3

Step A

To a suspension of (R)-2-Amino-3-(1H-indol-3-yl)-propionic acid 2 (0.23 g, 1.12 mmol) (Alfa-Aesar, A-18426) in acetone (3 mL) was added 2M sodium carbonate (1 mL) to stir at room temperature for 30 minutes. To this mixture was added bromosulfonyl chloride 1 (0.13 g, 0.5 mmol) (Alfa-Aesar, A-14677) at 0° C. to stir for 15 minutes. The reaction mixture was stirred further for 1 hour at room temperature. After pouring into water (20 mL), the solution was washed with ether (×3). The aqueous layer was acidified with 1M HCl, followed by extraction with ethyl acetate (×3). The combined organic extracts were then washed with brine and dried ($Na_2SO_4$) to provide the crude (R)-2-(5-Bromo-thiophene-2-sulfonylamino)-3-(1H-indol-3-yl)-propionic acid product (3) (0.16 g, 74%). LC-MS (ES+) 429, 431; (ES−) 427, 429.

A portion of the crude (R)-2-(5-Bromo-thiophene-2-sulfonylamino)-3-(1H-indol-3-yl)-propionic acid product (3) was taken to the next step without further purification.

Example 2: Synthesis of Compound 5

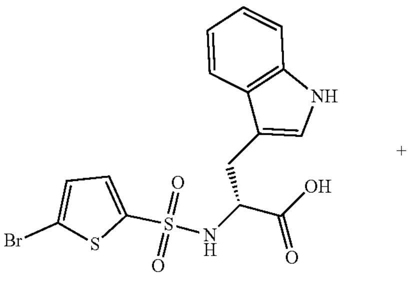

3

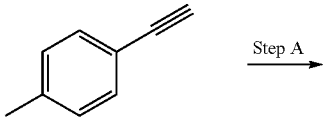

4

-continued

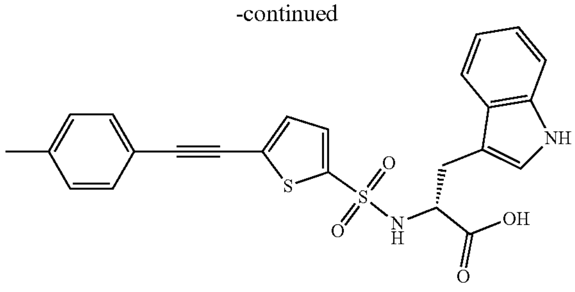

5

Step A

In a round bottom flask was added crude (R)-2-(5-Bromo-thiophene-2-sulfonylamino)-3-(1H-indol-3-yl)-propionic acid (3) (60 mg, 0.14 mmol), p-tolyl acetylene 4 (480 mg, 0.41 mmol), $PdCl_2P(PPh_3)_2$ (10 mg, 0.015 mmol), copper (I)iodide (2 mg, 0.01 mmol) and triethylamine (0.025 g, 0.25 mmol) and then dissolved in dry DMF (2 mL) under an atmosphere of nitrogen. The reaction mixture was then heated at 50° C. under a nitrogen atmosphere for 2 hours. The reaction mixture was then cooled to room temperature and diluted with ethyl acetate and washed with a solution composed of $NaCl/NaHCO_3/(NH_4)_2CO_3$/water (1:1:1:1) (×3), water, and then dried over sodium sulfate ($Na_2SO_4$). The crude product was purified using a SAX column to provide to give the desired (R)-3-(1H-Indol-3-yl)-2-(5-p-tolylethynyl-thiophene-2-sulfonylamino)-propionic acid 5 (0.036 g, 55%).

Example 2, Reaction A was repeated with same scale as above and then combined with the previous batch. The combined products were then further purified using preparative, reversed-phase-HPLC to give (R)-3-(1H-Indol-3-yl)-2-(5-p-tolylethynyl-thiophene-2-sulfonylamino)-propionic acid 5 having a purity of >95% by HPLC. LC-MS (ES+) 465; (ES−) 463; $^1H$ NMR (300 MHz, DMSO-d6) δ 2.35 (s, 3H), 2.86-2.94 (m, 1H), 3.08-3.16 (m, 1H), 3.96-4.40 (m, 1H), 6.93-7.50 (m, 11H), 8.67 (d, 1H, J=8.7 Hz), 10.83 (s, 1H).

Example 3: Synthesis of Compound 118

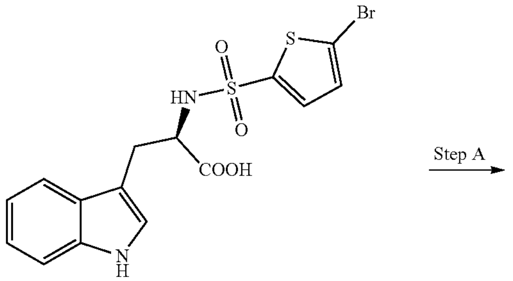

3

-continued

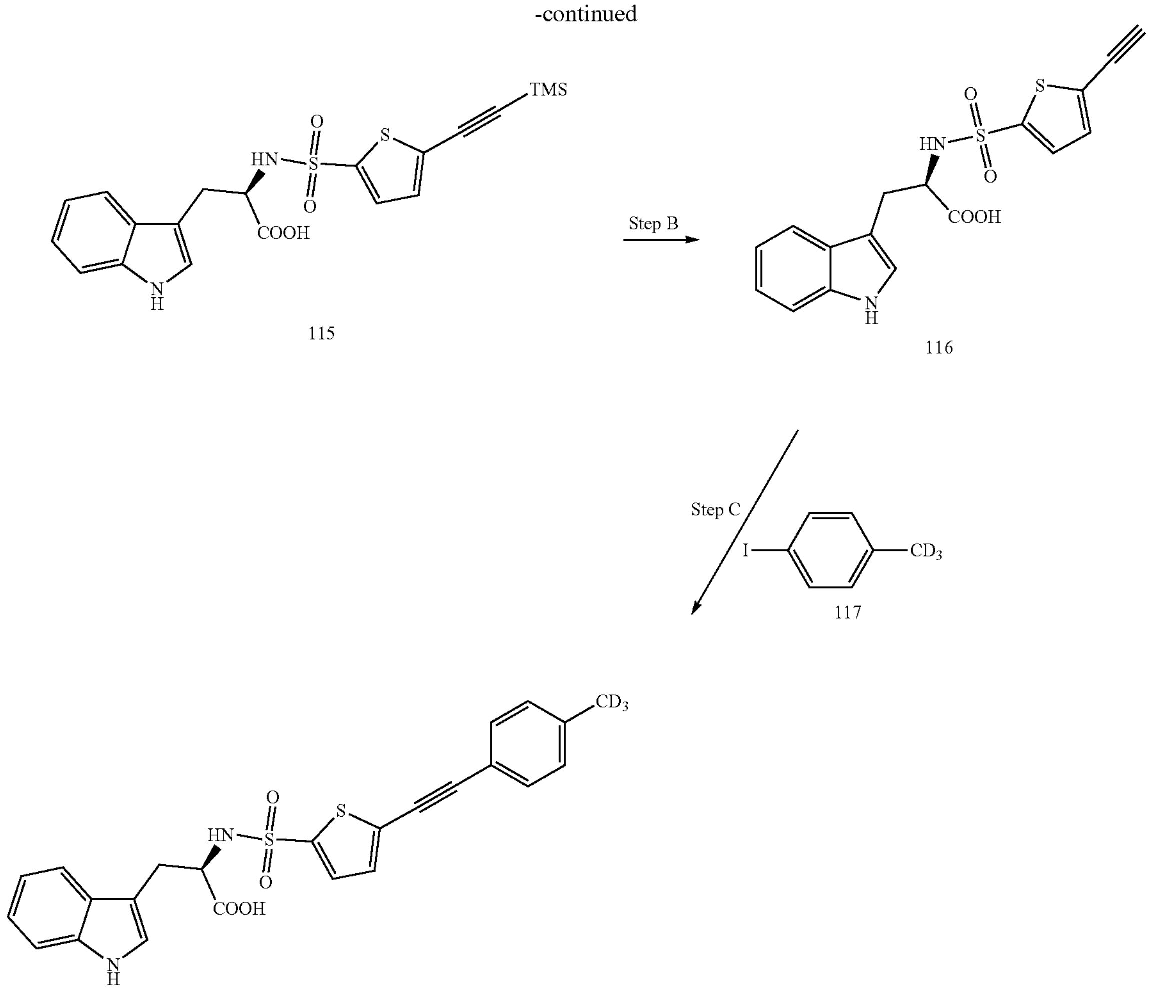

115 116 117 118

Step A

In a round bottom flask was added crude compound (R)-2-(5-Bromo-thiophene-2-sulfonylamino)-3-(1H-indol-3-yl)-propionic acid product (3) (0.25 g, 0.584 mmol) (synthesized via Example 1, Step A), commercially available ethynyltrimethylsilane (0.17 g, 1.73 mmol), $PdCl_2P(PPh_3)_2$ (0.041 g, 0.061 mmol), copper(I)iodide (0.006 g, 0.0315 mmol), and triethylamine (0.177 g, 1.75 mmol) dissolved in dry DMF (3 mL) under an atmosphere of nitrogen and mixture heated at 50° C. for two hours. The reaction mixture was then diluted with ethyl acetate and washed with a solution composed of $NaCl/NaHCO_3/(NH_4)_2CO_3$/water (1:1:1:1) (×3), water, brine, and dried ($Na_2SO_4$) to give the desired crude (R)-3-(1H-Indol-3-y1)-2-(5-trimethylsilanyl-ethynyl-thiophene-2-sulfonylamino)-propionic acid 115 (185 mg, 71%). LC-MS (ES+) 447; (ES−) 445.

Step B

To a solution of crude (R)-3-(1H-Indol-3-yl)-2-(5-trimethylsilanylethynyl-thiophene-2-sulfonylamino)-propionic acid 115 (0.126 g, 0.282 mmol) in dichloromethane/methanol mixture (1:1, 10 mL) was added $K_2CO_3$ (0.047 g, 0.34 mmol) and allowed to stir for 60 minutes. The reaction mixture was then filtered and retentate washed with dichloromethane-methanol mixture. The combined filtrate was concentrated under reduced pressure and then purified using a SAX column to obtain (R)-2-(5-Ethynyl-thiophene-2-sulfonylamino)-3-(1H-indol-3-yl)-propionic acid 116 (52 mg, 49%). LC-MS (ES+) 375; (ES−) 373.

Step C

In a round bottom flask was added (R)-2-(5-Ethynyl-thiophene-2-sulfonylamino)-3-(1H-indol-3-yl)-propionic acid 116 (0.052 g, 0.139 mmol), iodotoluene-(D3, 98%) 117 (0.061 g, 0.28 mmol) (obtained from commercially available 4-aminotoluene(D3, 98%) via Sandmeyer reaction outlined in Example 56), $PdCl_2P[(PPh_3)]_2$ (0.01 g, 0.015 mmol), copper(I)iodide (0.002 g, 0.0105 mmol) and triethylamine (0.025 g, 0.247 mmol) and dissolved in dry DMF (3 mL) under an atmosphere of nitrogen and mixture heated at 50° C. for 2 hours. The reaction mixture was cooled, diluted with ethyl acetate and washed with a solution composed of $NaCl/NaHCO_3/(NH_4)_2CO_3$/water (1:1:1:1) (×3), water, brine, and then dried over sodium sulfate ($Na_2SO_4$). The mixture was filtered and the filtrate was evaporated under reduced pressure to give crude 118 which was purified via SAX Column chromatography to give purified 118 (0.025 g, 38%). The product was further purified by preparative, reversed-phase-HPLC to obtain the desired product 118 (R)-3-(1H-Indol-3-yl)-2-[5-(4-trideuteromethyl-phenyl-ethynyl)-thiophene-2-sulfonylamino]-propionic acid-(D3, 98%) in >95% purity by HPLC. LC-MS (ES+) 468; (ES—) 466; $^1$H NMR (300 MHz, MeOH-d4) δ 3.17-3.25 (m), 4.32-4.35 (m), 5.60-5.66 (m), 7.05-7.68 (m), 10.4 (br s).

Example 4: Synthesis of 4-Iodotoluine (D3, 98%) Starting Material

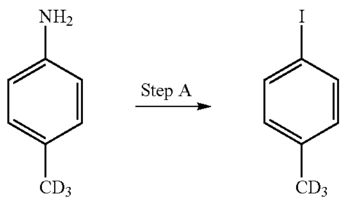

119 117

Step A

Following the classic method of Griess (Practical Organic Chemistry, Richard Clay & Sons, page 144, Preparation #60, (1900)) in which 0.2 grams (1.8 mmoles) of toluidine (D3, 98%), commercially obtained from C/D/N Isotopes (Quebec, Canada) (119) is combined with 0.4 ml $D_2SO_4$ (obtained commercially from Cambridge Isotope Laboratories, Andover, MA) and the resulting mixture cooled until the temperature of the stirred mixture reaches 0° C. and then 160 mg (2.32 mmole) of sodium nitrite was slowly added in three portions over 10 minutes making sure that the temperature does not rise above 10° C. After the sodium nitrite has been added, a solution composed of 48 mg (2.9 mmole) of KI in lml D20 (obtained commercially from Cambridge Isotope Laboratories) was then added and the reaction mixture was allowed to warm to room temperature and stirred for 1 hour. The reaction mixture was then diluted with D20 (10 mL) and extracted with ether (×2). The ether layer was then washed with 10% $Na_2S_2O_3$ in $D_2O$ (×2) and dried over anhydrous sodium sulphate. The crude product (117) was then purified by column chromatography using hexane as the eluent to obtain the desired pure 4-Iodotoluene (D3, 98%) product (117) (0.16 g, 40%). $^1H$ NMR (300 MHz, $CDCl_3$): δ, 6.93 (d, 2H, J=7.8 Hz), 7.56 (d, 2H, J=7.8 Hz). When the $D_2SO_4$ was replaced by DCl (obtained commercially from Cambridge Isotope Laboratories, Andover, MA) only a 20% yield of 117 was obtained.

Example 5: Synthesis of Deuterated Compound 82

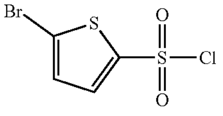

+

1

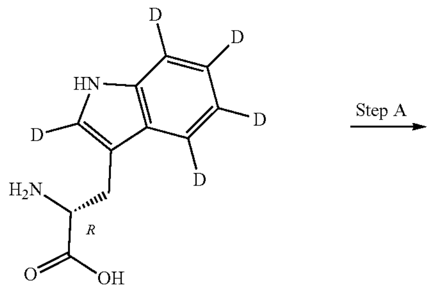

131

-continued

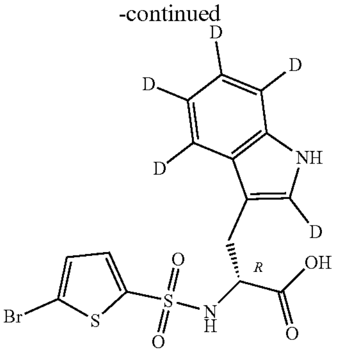

70

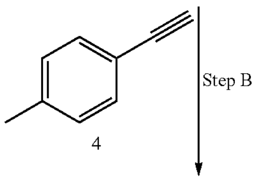

4

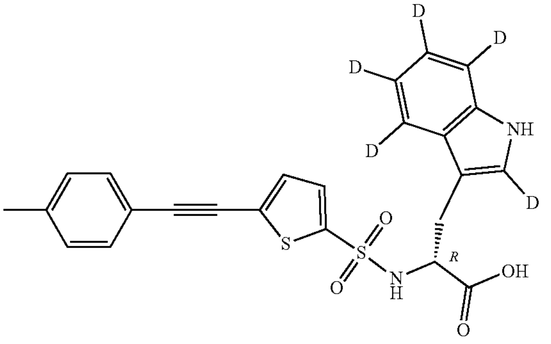

82

Step A

To a suspension of (R)-2-Amino-3-(2,4,5,6,7-pentadeutero1H-indol-3-yl)-propionic acid 131 (0.20 g, 0.95 mmol) (Commercially obtained from CDN Isotopes, Quebec, Canada, Cat. #D-7416) in acetone (7 mL) was added 2M sodium carbonate (2 mL) to stir at room temperature for 30 minutes. To this mixture was added bromosulfonyl chloride 1 (0.25 g, 0.96 mmol) (Alfa-Aesar, A-14677) at 0° C. to stir for 15 minutes. The reaction mixture was stirred further for 15 hours at room temperature. The reaction mixture was then poured into water (20 mL), the solution was washed with ether (×3). The aqueous layer was acidified with 1M HCl, followed by extraction with ethyl acetate (×3). The combined organic extracts were then washed with brine and dried ($Na_2SO_4$) to provide the crude (R)-2-(5-Bromo-thiophene-2-sulfonylamino)-3-(2,4,5,6,7-pentadeutero-1H-indol-3-yl)-propionic acid (70) (0.3 g, 73%). LC-MS (ES+) 434; (ES−) 432.

Step B

In a round bottom flask was added crude (R)-2-(5-Bromo-thiophene-2-sulfonylamino)-3-(2,4,5,6,7-pentadeutero-1H-indol-3-yl)-propionic acid (70) (0.3 grams, 0.69 mmol), p-tolyl acetylene 4 (90 mg, 0.71 mmol), $PdCl_2P(PPh_3)_2$ (16 mg, 0.023 mmol), copper(I)iodide (7 mg, 0.04 mmol) and triethylamine (0.21 g, 2.15 mmol) and then dissolved in dry DMF (2.5 mL) under an atmosphere of nitrogen. The reaction mixture was then heated at 50° C. under a nitrogen atmosphere for 20 hours. The reaction mixture was then cooled to room temperature and diluted with ethyl acetate and washed with a solution composed of $NaCl/NaHCO_3/(NH_4)_2CO_3$/water (1:1:1:1) (×3), water, and then dried over sodium sulfate ($Na_2SO_4$) to give crude R)-3-(2,4,5,6,7-Pentadeutero-1H-indol-3-yl)-2-(5-p-tolylethynyl-thiophene-2-sulfonylamino)-propionic acid 82 (0.1 g, 31%). A portion of the crude product was purified using preparative thin layer chromatography ($SiO_2$, 100 microns, 10% methanol in methylene chloride) to give ~50 mg of an oil with a Rf=0.5 ($SiO_2$, 40% ethylacetate-methylene chloride). The oil was crystallized with ether-methylene chloride (8:2) to give 10 mg of 82 as a white solid having a purity of >95% by HPLC. LC-MS (ES+) 470; (ES—) 468; $^1H$ NMR (300 MHz, DMSO-d6) δ 2.33 (s, 3H), 2.86-2.94 (m, 1H), 3.05-3.07 (m, 1H), 3.34-3.55 (m, 1H), 7.24 (d, 2H, J=7.8 Hz), 7.28 (d, 1H, J=3.9 Hz), 7.40 (d, 1H, J=3.9 Hz), 7.46 (d, 2H, J=7.8 Hz), 10.65 (s, 1H).

Synthesis of Ester and Amide Prodrugs

Prodrugs are substances administered in an inactive form that is then metabolized in the body in vivo into the active compound. The rationale behind administering prodrugs is to optimize absorption, distribution, metabolism, and excretion of these drugs. Prodrugs can be made from the carboxylic portion of the parent drug by converting them to the corresponding ester or amide.

Scheme 1

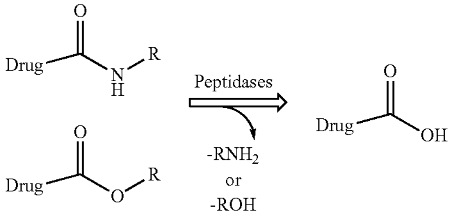

A variety of esterases, amidases, and/or peptidases in plasma or in other tissues can bioconvert these ester or amide prodrugs to their active counterparts (Scheme 1). Amino acid ester and amide prodrugs can sometimes be used to enhance absorption and consequently oral drug delivery of the parent carboxylic acid containing drug, because the brush-border membrane (microvilli-covered surface) of intestinal epithelium possesses a considerable number of transporters for amino acids and peptides.

Example 6: Synthesis of an Activated Ester Prodrug of Compound 5

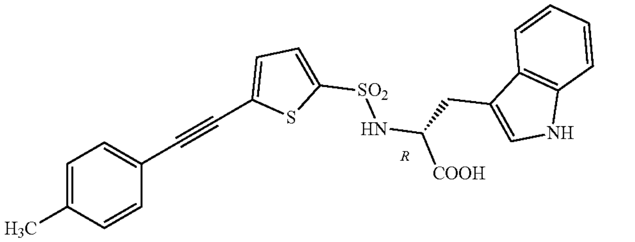

5

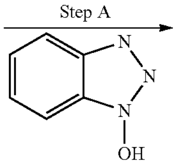

140

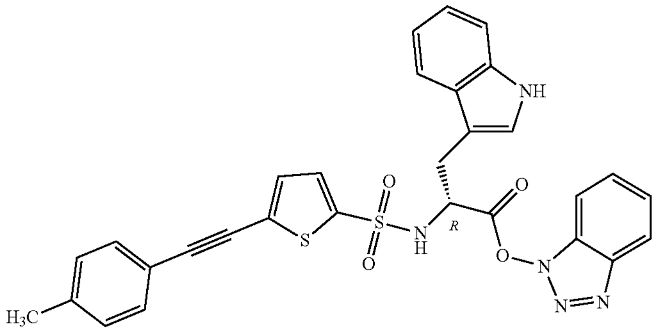

141

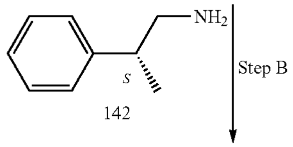

142

-continued

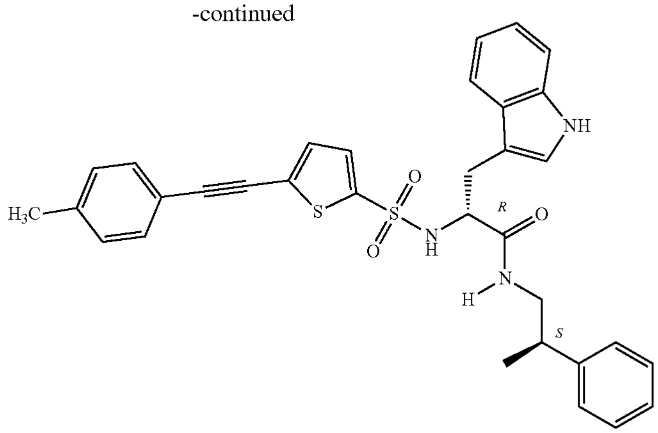

143

Step A

To a 10 ml round bottom flask containing a stir bar was added (R)-3-(1H-Indol-3-yl)-2-(5-p-tolylethynyl-thiophene-2-sulfonylamino)-propionic acid 5 (37 mg, 0.08 mmole), hydroxybenzotriazol 140 (HOBT, 13 mg, 0.09 mmole) and (1-[Bis(dimethylamino)methylene]-1H-1,2,3-triazolo[4,5-b]pyridinium 3-oxid hexafluorophosphate) (HATU, 29 mg, 0.07 mmole) and mixture put under vacuum then under nitrogen. To the solid was then added 0.8 ml of dimethylformamide (DMF) and 25 microliters (0.14 mmole) of diisopropylethylamine (DIEA) and mixture stirred under nitrogen for 25 minutes to give in-situ crude 141. To the reaction mixture was then added (s)-beta-methylphenethylamine 142 (15 microliters, 0.1 mmole) and mixture stirred for 3 hours. The reaction mixture was diluted with 50 ml of methylene chloride and organic layer washed with 50 ml of 10% aqueous hydrochloric acid and then 50 ml of saturated sodium bicarbonate. The organic layer was then separated and dried over magnesium sulfate, filtered and the volatile components removed under reduced pressure to give crude 3-(1H-Indol-3-yl)-N-(2-phenyl-propyl)-2-(5-p-tolylethynyl-thiophene-2-sulfonylamino)-propionamide 143 as an oil. (50 mg crude weight). LC-MS (ES+) 582; (ES+Na) 604. A portion of crude 143 was purified by preparative thin layer chromatography (prep-TLC, $SiO_2$, 5% methanol-methylene chloride) to give 15 milligrams pure 143 as a light tan solid $R_f$=0.4 ($SiO_2$, 5% methanol in methylene chloride). $^1H$ NMR (300 MHz, Methanol-d4) δ 1.07 (d, 3H, J=6.0 Hz), 2.37 (s, 3H), 2.6-2.82 (m, 2H), 3.29-3.30 (m, 2H), 4.00 (dd, 2H, J=6 Hz, J=6 Hz), 6.8-7.46 (m, 16H).

Example 7: Synthesis of Racemic Compound 5

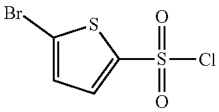

1

+

-continued

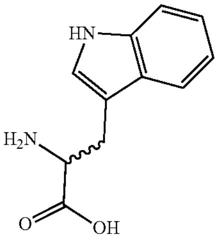

147

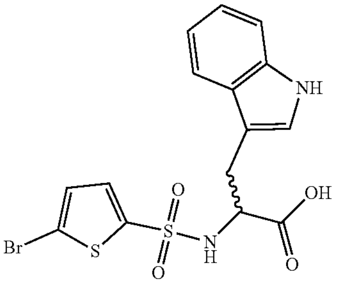

148

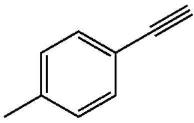

4

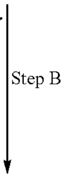

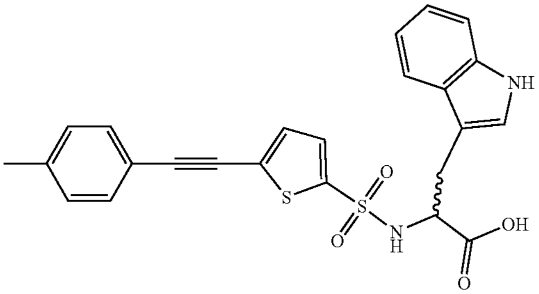

149

Step A

To a suspension of racemic tryptophan 147 (0.62 g, 3.0 mmol) (Commercially obtained from Alfa Aesar) in acetone (10 mL) was added 2M sodium carbonate (2.4 mL) to stir at room temperature for 30 minutes. To this mixture was added bromosulfonyl chloride 1 (0.35 g, 1.34 mmol) (Alfa-Aesar, A-14677) at 0° C. to stir for 15 minutes. The reaction mixture was stirred further for 1 hour at room temperature. The reaction mixture was then poured into water (30 mL), the solution was washed with ether (×3). The aqueous layer was acidified with 1M HCl, followed by extraction with ethyl acetate (×3). The combined organic extracts were then washed with brine and dried ($Na_2SO_4$) to provide the crude Racemic 3-(1H-Indol-3-yl)-2-(5-p-tolylethynyl-thiophene-2-sulfonylamino)-propionic acid (148) (0.47 g, 82%). LC-MS (ES+) 429; (ES−) 427.

Step B

In a round bottom flask was added crude, racemic 3-(1H-Indol-3-yl)-2-(5-p-tolylethynyl-thiophene-2-sulfonylamino)-propionic acid (148) (0.43 grams, 1.02 mmol), p-tolyl acetylene 4 (0.15 g, 1.26 mmol), $PdCl_2P(PPh_3)_2$ (16 mg, 0.023 mmol), copper(I)iodide (14 mg, 0.08 mmol) and triethylamine (0.37 g, 2.8 mmol) and then dissolved in dry DMF (6 mL) under an atmosphere of nitrogen. The reaction mixture was then heated at 50° C. under a nitrogen atmosphere for 15 hours. The reaction mixture was then cooled to room temperature and the volatile components removed under reduced pressure to crude racemic 3-(1H-Indol-3-yl)-2-(5-p-tolylethynyl-thiophene-2-sulfonylamino)-propionic acid 149 as a brown oil. The crude oil was purified by column chromatography (SiO2, 30% ethylacetate-hexane) to give an oil which was recrystallized from methanol to give 60 mg of 149 as a white solid (13%) having a purity of >95% by HPLC. LC-MS (ES+) 465; (ES−) 463; $^1H$ NMR (300 MHz, DMSO-d6) δ 2.47 (s, 3H), 2.97 (q, 1H, J=8.9 Hz), 3.0 (q, 2H, J=5.7 Hz), 3.95 (br. m, 1H), 6.95-7.4 (m, 9H), 7.46 (d, 2H, J=7.8 Hz), 8.70 (br s., 1H), 10.65 (s, 1H).

Example 8: Synthesis of an Activated Ester Prodrug of Racemic Compound 151

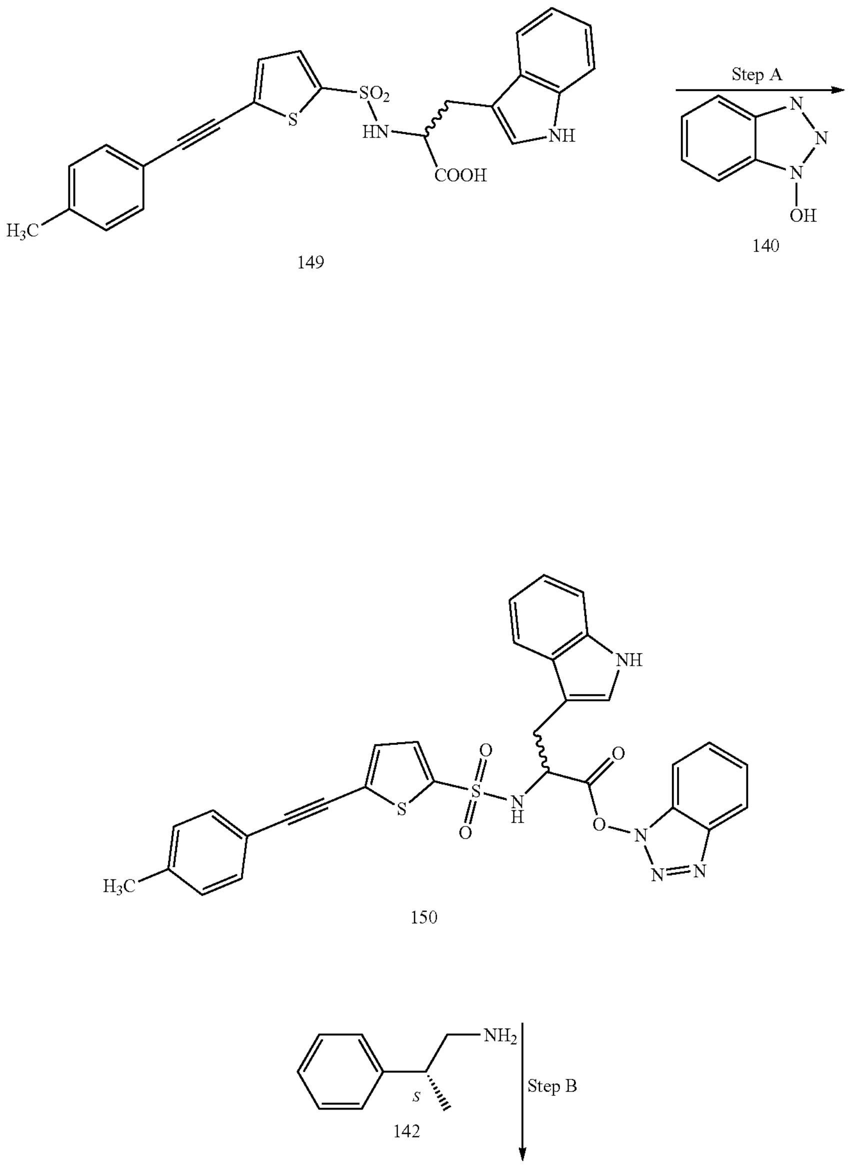

149

140

150

142

-continued

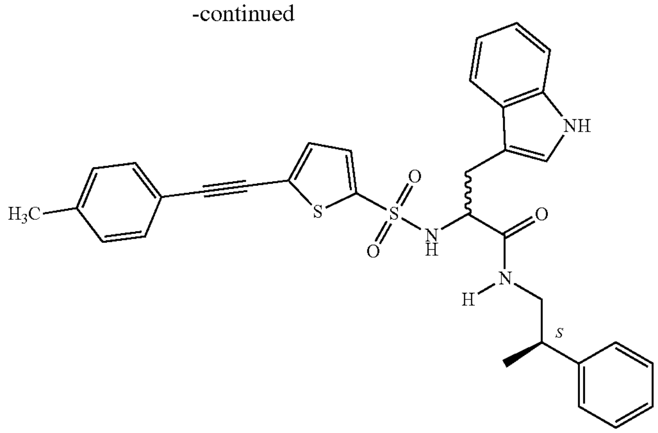

151

Step A

To a 10 ml round bottom flask containing a stir bar was added crude racemic 3-(1H-Indol-3-yl)-2-(5-p-tolylethynyl-thiophene-2-sulfonylamino)-propionic acid 149 (37 mg, 0.08 mmole), hydroxybenzotriazol 140 (HOBT, 13 mg, 0.09 mmole) and (1-[Bis(dimethylamino)methylene]-1H-1,2,3-triazolo[4,5-b]pyridinium 3-oxid hexafluorophosphate) (HATU, 29 mg, 0.07 mmole) and mixture put under vacuum then under nitrogen. To the solid was then added 0.8 ml of dimethylformamide (DMF) and 25 microliters (0.14 mmole) of diisopropylethylamine (DIEA) and mixture stirred under nitrogen for 25 minutes to give in-situ crude 150. To the reaction mixture was then added (s)-beta-methylphenethyl-amine 142 (15 microliters, 0.1 mmole) and mixture stirred for 3 hours. The reaction mixture was diluted with 50 ml of methylene chloride and organic layer washed with 50 ml of 10% aqueous hydrochloric acid and then 50 ml of saturated sodium bicarbonate. The organic layer was then separated and dried over magnesium sulfate, filtered and the volatile components removed under reduced pressure to give crude 3-(1H-Indol-3-yl)-N-(2-phenyl-propyl)-2-(5-p-tolylethynyl-thiophene-2-sulfonylamino)-propionamide 151 as an oil (crude ~80 mg). LC-MS (ES+) 582; (ES+Na) 604. A portion of crude 151 was purified by preparative thin layer chromatography (prep-TLC, $SiO_2$, 5% methanol-methylene chloride) to give 10 milligrams pure 151 as a light tan solid $R_f$=0.38 (SiO2, 5% methanol in methylene chloride). $^1H$ NMR (300 MHz, Methanol-d4) δ 1.10 (dd, 3H, J=7.2 Hz, J=20 Hz), 2.38 (s, 3H), 2.6-2.80 (m, 2H), 3.29-3.32 (m, 2H), 4.02 (dd, 2H, J=6 Hz, J=6 Hz), 6.75-7.43 (m, 16H).

Example 9: Synthesis of Sodium Salt of Compound 5

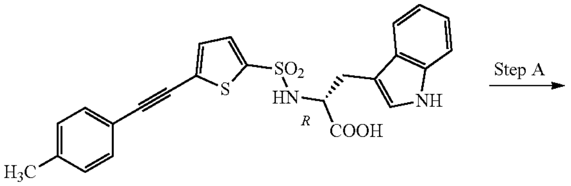

5

-continued

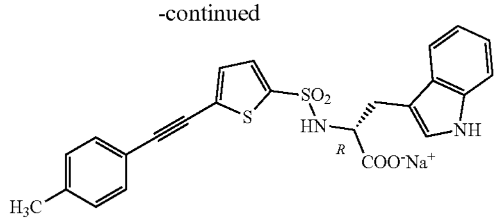

Sodium Salt

Step A

Crude Compound 5 (300 grams) was dissolved in 3 liters of tetrahydrofuran (THF) and washed with brine (500 ml) then the batch was then reheated to 40° C. and washed with aqueous acetyl cysteine (82 g) in water (500 ml) for 1 hr. After cooling to <35° C., the batch was left to settle for 15 min and 0.4 L aqueous separated out. The batch was then washed with brine (500 ml) for 15 min and left to settle for 15 min. 0.8 L of aqueous was separated out. The batch was then washed with brine (500 ml) and after settling, 0.6 L aqueous was separated out. The organic phase was then washed with 2 M potassium carbonate solution (250 ml) at 20° C. for 10 min and then allowed to settle. 0.3 L aqueous separated out. The batch was then washed twice with brine (500 ml×2) with 0.6 L and 0.5 L removed respectively. The organic layer was then heated back to 40° C. Heptane (1.7 L) was then added over 30 min. Crystallization started slowly on the sides of the reactor. After 1.4 L of the 1.7 L of hexane had been added, solids were visible in the bulk. The remainder of the heptane (0.3 L) was then added and cooling started. When the batch reached 30° C., it looked thinner (less precipitate) than normal, and so an additional heptane (0.3 L, 2 L total) was added. The batch was then cooled to 4° C. and filtered in two portions (due to filter size). Each portion was washed with fresh heptane (2×0.5 L) and pulled dry on the filter. The combined material was dried under vacuum at 60° C. overnight to give 266 g of 97% pure Compound 5 as the sodium salt. Elemental Analysis sodium salt monohydrate, theoretical C, 57.13; H, 4.20; N, 5.55; Found: C 57.1; H, 4.2; N 5.7. Water by KF titration=3.8%. X-ray fluorescence results for Compound 5 (Average of 5 replicates (% w/w)) indicate 6.3% sodium by weight.

Example 10: Measuring the Level of Caspase 3 in Rat Tissue Via Western Blotting Western blotting is a widely used analytical technique used to detect specific proteins in a sample of tissue homogenate or extract. Before one can perform Western blotting one must develop a technique for extracting the protein to be measured from the target tissue. Below is an example of the measurement of Caspase 3 from rat dorsal root ganglion (DRG) using Western blotting.

Protein Extraction Preparation: Frozen DRG tissue samples were homogenized in a radioimmunoprecipitation assay (RIPA) buffer (75 μl per sample) using a handheld pestle homogenizer, 30 seconds on ice. Samples were cleared by centrifugation at 14,000 rpm for 15 minutes at 4° C. Supernatants were collected and protein amount was determined using Bio-Rad DC protein kit.

Western Blotting: Protein samples were denatured in Laemmli buffer/2-mercaptoethanol for 5 minutes at 95 C. Denatured protein samples were separated by SDS-PAGE. After electrophoresis, proteins were transferred from gel to LFP-PVDF membranes by electroblotting. Non-specific binding of antibodies was blocked with 5% w/v dried milk in 1×TBST for one hour. After a brief rinse in TBST, the blots were probed with primary antibody prepared with 1% w/v milk in 1×TBST at 4° C. overnight. Protein-PVDF blots were washed once for 15 minutes followed by 3 more 5 minutes washes with TB ST. Protein-PVDF blots were then incubated with the appropriate secondary antibody prepared with 1% milk in TBST for 1 hour at room temperature. Protein-PVDF blots were washed once for 15 minutes followed by one more wash for 5 minutes.

| Protein Target | Protein Molecular Weight | Vendor | Catalog # |
|---|---|---|---|
| Caspase 3 | 11, 17, 20 kDa | Santa Cruz Biotechnology | Sc-7148 |

Antibody binding was detected using the ECL Plus Western Chemifluorescence Detection Kit (Cat #32132, ThermoFisher Scientific). The detection solution was made fresh according to manufacturer's directions and dispensed onto membranes. After 5 minutes incubation, the protein-PDVF membranes were scanned using Typhoon 9410 scanner (GE Healthcare Bioscience) using 457 nm blue laser for excitation and 520 nm emission filter at 400V. The scanned images from the Typhoon were analyzed with ImageQuantTL software version 7.0 (GE Healthcare Bioscience, Piscataway, NJ). Band intensities were determined using the Rolling Ball method. Each protein target was first normalized to in lane housekeeping protein GAPDH (from the same gel). Normalized protein target for each sample was presented as ratio relative to Sham vehicle group.

Example 11: Measuring the Level of Caspase 3 in Rat Plasma Via ELISA

Enzyme-linked immunosorbent assay (ELISA) is a plate-based assay technique designed for detecting and quantifying substances such as peptides, proteins, antibodies and hormones. Below is an example of the measurement of Caspase 3 from rat plasma using ELISA. Each well of the supplied microtiter plate (Rat CASP3/Caspase 3 ELISA kit, Catalog No. LS-F11016, supplied by LifeSpan BioSciences, Inc.) has been pre-coated with a target specific capture antibody. Standards or samples are added to the wells and the target antigen binds to the capture antibody. Unbound Standard or sample is washed away. A biotin-conjugated detection antibody is then added which binds to the captured antigen. Unbound detection antibody is washed away. An Avidin-Horseradish Peroxidase (HRP) conjugate is then added which binds to the biotin. Unbound Avidin-HRP conjugate is washed away. A TMB substrate is then added which reacts with the HRP enzyme resulting in color development. A sulfuric acid stop solution is added to terminate color development reaction and then the optical density (OD) of the well is measured at a wavelength of 450 nm±2 nm. The OD of an unknown sample can then be compared to an OD standard curve generated using known antigen concentrations in order to determine its antigen concentration. Sample collection: Rat plasma was collected using heparin or EDTA as an anticoagulant. The tubes were centrifuged for 15 minutes at 1000×g at 2-8° C.

Assay Procedure: All of the reagents and samples were brought to room temperature without additional heating and mixed thoroughly by gently swirling before they were pipetted. All the reagents, working standards, and samples were prepared as directed in the kit instructions (Rat CASP3/Caspase 3 ELISA kit, Catalog No. LS-F11016, supplied by LifeSpan BioSciences, Inc.). The following procedure was the followed:

1. Add 100 μl of Standard, Blank, or Sample per well, cover with a plate sealer, and incubate for 2 hours at 37° C.
2. Aspirate the liquid of each well, do not wash.
3. Add 100 μl of Detection Reagent A working solution to each well, cover with a plate sealer, and gently agitate to ensure thorough mixing. Incubate for 1 hour at 37° C.
4. Aspirate the liquid from each well and wash 3 times. Wash by adding approximately 350 μl of 1× Wash Buffer using a squirt bottle, multi-channel pipette, manifold dispenser or automated washer. Allow each wash to sit for 1-2 minutes before completely aspirating. After the last wash, aspirate to remove any remaining Wash Buffer then invert the plate and tap against clean absorbent paper.
5. Add 100 μl of Detection Reagent B working solution to each well, cover with a new plate sealer, and incubate for 60 minutes at 37° C.
6. Aspirate the liquid from each well and wash 5 times as outlined in step 4.
7. Add 90 μl of TMB Substrate solution to each well, cover with a new plate sealer, and incubate for 15-30 minutes at 37° C. Protect from light and monitor periodically until optimal color development has been achieved.
8. Add 50 μl of Stop Solution to each well. The blue color will change to yellow immediately. If color change does not appear uniform, gently tap the plate to ensure thorough mixing. The Stop Solution should be added to wells in the same order and timing as the TMB Substrate solution.
9. Determine the optical density (OD value) of each well immediately using a microplate reader set to 450 nm.

Calculations: Average the duplicate readings for each standard, control, and sample and subtract the average zero standard optical density. Create a standard curve by reducing the data using computer software capable of generating a four-parameter logistic (4-PL) curve-fit. As an alternative, construct a standard curve by plotting the mean absorbance for each standard on the x-axis against the concentration on the y-axis and draw a best fit curve through the points on the graph. The data may be linearized by plotting the log of the target antigen concentrations versus the log of the O.D. and the best fit line can be determined by regression analysis.

Use of a commercial software program such as CurveExpert is recommended for performing these calculations. This procedure will produce an adequate but less precise fit of the data. If samples have been diluted, the concentration read from the standard curve must be multiplied by the dilution factor.

Calculation of results: Average. The duplicate readings for each standard, control, and sample were averaged and subtracted from the average zero standard optical density. A standard curve created by reducing the data using computer software capable of generating a four-parameter logistic (4-PL) curve-fit. The data was also linearized by plotting the log of the target antigen concentrations versus the log of the O.D. and the best fit determined by regression analysis.

Example 12: Measuring the mRNA Expression Level of Caspase 3 in Rat Tissue Via Real Time Quantitative Polymerase Chain Reaction (RT-qPCR)

The real-time reverse transcription polymerase chain reaction (RT-PCR) addresses the evident requirement for quantitative data analysis in molecular medicine, biotechnology, microbiology and diagnostics and has become the method of choice for the quantification of mRNA. Quantitative polymerase chain reaction (qPCR), also called real-time polymerase chain reaction, is a laboratory technique of molecular biology based on the polymerase chain reaction (PCR), which is used to amplify and simultaneously quantify a targeted.

RNA and cDNA preparation: Tissue samples were homogenized 2×1 min at 25 Hz in 750 μL of QIAzol Lysis Reagent (Cat #79306, Qiagen, Valencia, CA) with TissueLyser (Qiagen, Valencia, CA) and 5 mm stainless steel beads (Cat #69989, Qiagen, Valencia, CA). Disrupted samples were incubated at room temperate for 5 minutes. For RNA extraction, manufacturer protocol for RNeasy 96 Universal Tissue Kit (Cat #74881, Qiagen, Valencia, CA) for RNA isolation was followed. Briefly, 150 μL of Chloroform (Cat #C2432, Sigma-Aldrich, St. Louis, MO) was added and samples were shaken vigorously for 15 seconds followed by 3-minute incubation at room temperature. The aqueous phase was separated from the organic phase by centrifugation at 6,000×g (Beckman Coulter Avanti J-301), 4° C. for 15 minutes. The aqueous phase was then transferred to a new 96-well block and total RNA was precipitated with equal volume of 70% ethanol and then transferred to a RNeasy 96-well plate followed by centrifuge at 6,000-×g (Beckman Coulter Avanti J-301), at room temperate for 4 minutes. Total RNA bound to column membranes was treated with RNase-Free DNase set (Cat #79254, Qiagen, Valencia, CA) for 30 minutes, followed by 3 washing steps with RW1 and RPE buffers (provided with RNeasy 96 Universal Tissue Kit). RNA were eluted with 20 μL RNase-Free water. RNA was quantified using Nanodrop 8000. Total RNA (0.5 μg of RNA) was reverse transcribed into cDNA with 3.2 μg random hexamers (Cat #11034731001, Roche Applied Science, Indianapolis, IN), 1 mM each dNTP (Cat #11814362001), Roche Applied Science, Indianapolis, IN), 20U Protector RNase Inhibitor (Cat #03335402001, Roche Applied Science, Indianapolis, IN), 1× Transcriptor Reverse Transcription reaction buffer and 10U Transcriptor Reverse Transcriptase (Cat #03531287001, Roche Applied Science, Indianapolis, IN) in 204, total volume. The reactions were allowed to proceed at room temperature for 10 minutes, 55° C. for 30 minutes, then inactivated at 85° C. for 5 minutes in GeneAmp PCR Systems 9700 thermal cycler (Applied Biosystems, Foster City, CA). cDNA samples were diluted 10 folds with RNase-Free water for qPCR analysis.

qPCR: All qPCR reagents and TaqMan Expression Assays were purchased from ThermoFisher Scientific. Briefly, 5 μl of diluted cDNA was amplified with qPCR primer and probe sets in 1× TaqMan Fast Advanced Master Mix in 20 μl final reaction volume. Reactions were run on Applied Biosystems 7900HT Fast Block System with the following parameters: 95° C. for 20 s; 40 cycles of [95° C./3 s; 60° C./30 s]. Each cDNA sample was run in triplicates.

Standard curve calculation: The Ct value for serially diluted pooled (SNL) cDNA was plotted against the log value of dilution factor and the slope of the linear regression was determined. Please note that only assays with $r^2$ values greater than 0.95 were used in this study. PCR efficiency was calculated as follows:

$$\text{PCR Efficiency}=10^{-1/slope}$$

The relative mRNA expression for each target was calculated as follows:

$$\Delta Ct_{sample} \text{ for Target}=Ct\ \text{Target}_{control}-Ct\ \text{Target}_{sample}$$

$$\Delta Ct_{sample} \text{ for GAPDH}=Ct\ \text{GAPDH}_{control}-Ct\ \text{GAPDH}_{sample}$$

Normalizing Target to GAPDH for each sample=

$$\text{PCR Efficiency Target}^{(\Delta Ctsample\ for\ Target)}$$

$$\text{PCR Efficiency GAPDH}^{(\Delta Ctsample\ for\ GAPDH)}$$

Normalized target expression will be expressed relative to the average of Sham group.

Example 13: Measuring Caspase 3 Enzymatic Activity Levels in Fluids and Tissues One technique to determine if the level of caspase 3 is elevated is to measure the activity of the both procaspase 3 and of caspase 3 in both fluids and tissues and compare to controls. A standard way to do this is via a fluorometric assay that was developed by Hasegawa and co-workers (Cancer Research, 56, 1713-1718, 1996). A kit can be purchased from a commercial supplier such as BioVision. Activation of procaspse 3 and/or caspase 3 initiates apoptosis in mammalian cells. The CPP32/Caspase-3 Fluorometric Protease Assay Kit from BioVision provides a simple and convenient means for assaying the DEVD-dependent caspase activity. The assay is based on detection of cleavage of substrate DEVD-AFC (AFC: 7-amino-4-trifluoromethyl coumarin). DEVD-AFC emits blue light (λmax=400 nm); upon cleavage of the substrate by procaspase 3 and/or caspase 3, free AFC emits a yellow-green fluorescence (λmax=505 nm), which can be quantified using a fluorometer or a fluorescence microtiter plate reader. Comparison of the fluorescence of AFC from an apoptotic sample with an uninduced control allows determination of the fold increase in caspase-3 activity.

Procedure: Peptide, DEVD-AFC, was purchased from a commercial vendor (BioVision). Lysates were centrifuged at 15,000 rpm for 3 min, and cleared supernatants were collected. Protein concentrations were adjusted to 30 microgram/ml. Aliquots (2 ml) were incubated with DEVD-AFC (50 microMole) 37° C. for 1-2 hours and the release of 7-amino-4-trifluoromethyl coumarin was monitored by a spectrofluorometer (Hitachi F-3000) using an excitation wavelength of 400 nm and an emission wavelength off 505 nm. One unit was defined as the amount of enzyme required to release 0.22 nmol AFC per minute at 37° C.

Example 14: Measuring Caspase 3 Protein Levels and Location Using Immunohistochemistry (IHC)

Immunohistochemistry (IHC) is a method for detecting the location of proteins and other antigens in tissue sections using antibodies. In general, IHC data provide a valuable perspective that can help interpret data obtained using other methods. The key to high quality immunohistochemical staining is the specificity of the antibody used. A highly specific antibody will bind only to the protein of interest in the tissue section. The antibody-antigen interaction is visualized using either chromogenic or fluorescent detection. In chromogenic detection, the antibody is conjugated to an enzyme that cleaves a substrate to produce a colored precipitate at the location of the protein. In fluorescent detection, the antibody is conjugated to a fluorophore that can be visualized using fluorescence microscopy. IHC is routinely used to visualize the location and semi quantify the level of both procaspase 3 and caspase 3 in tissues (i.e. brain, spinal cord, nerve et al.). Following the methods of Gown and Willingham (the Journal of Histochemistry & Cytochemistry, 50(4), 449-454, 2002) and Hoffmann and coworkers (Tissue Engineering, Part C, 20(2), 91-103, 2014), caspase 3 can be measured in both brain and nerve tissue. Below is but one example of a procedure that was followed.

Sections from the biopsy specimens (brain and spinal tissue) were formalin-fixed and paraffin-embedded. For IHC examination, slides from the spinal cord and sciatic nervous were evaluated for caspase-3 (cas-3). Serial 3-5-μm thick sections were cut from paraffin embedded tissue blocks. For subsequent IHC staining glass slices were exposed to hot unmasking fluidized citrate buffer pH 6.0 for 15-18 min. After cooling, the glass with the slice was transferred into phosphate-buffered saline (PBS) pH 7.4. The sections were deparaffinized and then rehydrated in alcohol to tris-buffered saline. Endogenous peroxidase activity was blocked using 3% hydrogen peroxide followed by a protein block with 5% goat serum.

Affinity purified monoclonal $IgG_1$, Caspase-3 p11 antibodies (sc-271759; Santa Cruz BioTechnology Inc., Dallas, TX, USA) were used as the primary antibody and applied at a 1:50 dilution 100 μl/glass for 30 min at room temperature. Labeled streptavidinbiotin (LSAB) was used for the detection system with diaminobenzidine tetrahydrochloride (DAB) as the chromogen.

All sections were washed in PBS, examined under Olympus BX51 microscope and photographed with Carl Zeiss Axio Scope A1 light microscope with digital camera AxioCamlCc 1 at ×100, ×200, ×400 and ×1000 magnifications.

Example 15: In-Vivo Oral Rat Pharmacokinetics (PK) in Sprague-Dawley Rats

Understanding the pharmacokinetics in species typically employed in preclinical animal testing is an essential component of drug discovery. Select compounds of the present disclosure were orally dosed in rats in order to determine their relative oral bioavailability to demonstrate that the compounds of the present disclosure are orally bioavailable. Procedure: Six (6) male Sprague-Dawley rats were used. Fasting was conducted at least 16 hours prior to dose administration. Food was returned at approximately 4 hours post dose. The animals were placed into 2 groups of 3 animals per group. The oral (PO) formulation for Groups 1 & 2 were prepared on the day of dosing at a target concentration of 0.5 mg/mL in 0.5% Methylcellulose (400 cps) to produce a white, homogeneous suspension. Dosing was performed as outlined in Table 1:

TABLE 1

In vivo Rat PK Study Protocol via Oral (PO) Administration of Select Compounds.

| Group | No. of Male Rats | Compound Structure/ID# | | Dose (mg/Kg) | Dose Volume (mL/kg) | Vehicle | Route |
|---|---|---|---|---|---|---|---|
| 1 | 3 | 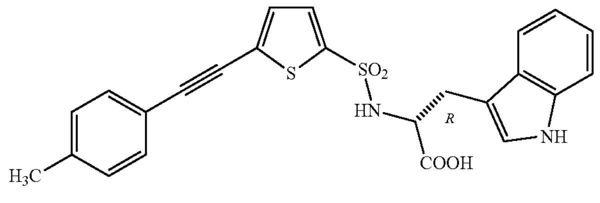 | 5 | 10 | 2 | 0.5% MC | PO |
| 2 | 3 | 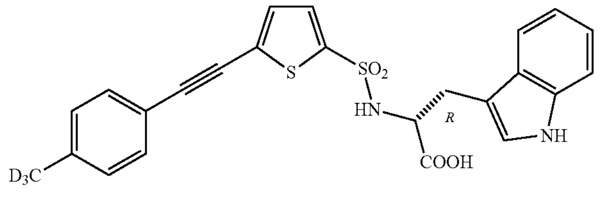 | 118 | 10 | 2 | 0.5% MC | PO |

Conc. = concentration; MC = Methylcellulose; PO = oral by gavage

Each animal in Group 1 received prepared compound (5) by oral dose administration at a target dose level of 1.0 mg/kg and at a dose volume of 2 mL/kg. Each animal in Group 2 received prepared compound (118) by oral dose administration at a target dose level of 1.0 mg/kg and at a dose volume of 2 mL/kg (Table 1). Whole blood samples (0.250 mL; $K_2$EDTA anticoagulant) were collected from each animal through a jugular vein catheter. Whole blood samples were collected from all animals pre-dose, and at 0.25, 0.5, 1, 2, 4, 8, 16, and 24 hours after dose administration. All blood samples were immediately placed on ice until processing. Whole blood samples were centrifuged at 2200×g for 10 minutes in a refrigerated centrifuge (5±3° C.) to isolate plasma. The plasma samples were transferred to individual polypropylene vials and immediately placed on dry ice before storage at nominally −20±5° C. The plasma samples sometime later were then thawed and extracted and analyzed by high pressure liquid chromatography (HPLC) coupled to Mass Spectrometry (MS) (Table 2). Pharmacokinetic parameters (Table 3) were estimated using WinNonlin® pharmacokinetic software (Version No. 5.2.1) using a non-compartmental approach consistent with the PO route of administration. Pharmacokinetic results of select compounds are presented in Table 3.

TABLE 2

Definition of PK Parameters & HPLC-MS Conditions.

| Parameter | Description of Parameter or Conditions |
|---|---|
| AUC(0-t) | The area under the concentration versus time curve from time zero to the time after dosing at which the last quantifiable concentration of the drug was observed; estimated by the linear or linear/log trapezoidal method. |
| T½ | The apparent terminal elimination half-life. |
| AUC(0-inf) | The area under the arithmetic mean concentration versus time curve from time zero to infinity. |
| Cmax | Maximum observed concentration, occurring at Tmax. |
| Tmax | Time of maximum observed concentration. For non-steady state data, the entire curve is considered. |
| LC Conditions & MS Instrument | Agilent 1200 Series Binary Pump, Leap CTC PAL autosampler, supelco Discovery C18 column (50 × 2.1 mm), mobile phase: water (0.1% formic acid) and acetonitrile (0.1% formic acid); A 1.0 min gradient was utilized going from 1% to 98% of Mobile Phase B for a total run time of 2.40 minutes. The mass spectrometer was an API 5000 |

TABLE 3

Mean PK Results for Oral (PO) Administration of Select Compounds in Male Sprague-Dawley Rats.

| Compound Structure/ID# | Dose level (mg/kg) | AUC(0-t) (ng•hr/mL) | AUC (0-inf) (ng•hr/mL) | T1/2 (hr) | Cmax (ng/mL) |
|---|---|---|---|---|---|
| 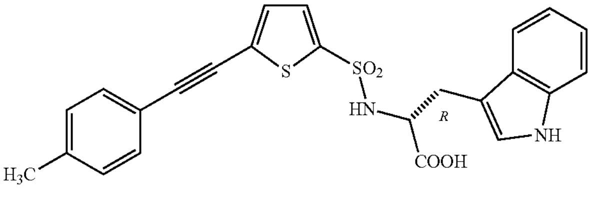 5 | 10 | 5117 | 5150 | 1.28 | 1580 |
| 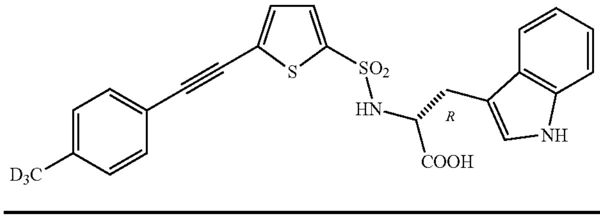 118 | 10 | 7681 | 7733 | 1.47 | 2740 |

Example 16: Steady State In-Vivo Oral Rat Pharmacokinetics (PK) and Compound Penetration into Spine and Brain It is important if one is observing biochemical effects in the spine and brain that one is able to show clear evidence that the compound being tested is in fact able to penetrate to those areas of the body. The present example orally doses compound 118 once per day (SID) for three days to a series of rats. On the third after dosing the rats were then sacrificed after taking blood samples and the level of compound measured in the spine and brain.

Procedure: Twelve (12) male Sprague-Dawley rats were used. Fasting was conducted at least 16 hours prior to dose administration. The animals were placed into 4 groups of 3 animals per group. There was one intravenous (IV) group and three oral gavage (PO) groups (10 mg/Kg, 20 mg/Kg & 40 mg/Kg). The oral (PO) formulation for Groups 2-4 were prepared on the day of dosing at a target concentration of 0.5 mg/mL in 0.5% Methylcellulose (400 cps) to produce a white, homogeneous suspension. The study design is outlined in Table 4:

TABLE 4

In vivo Rat PK Study Protocol via Oral (PO) Administration of Compound 118.

| Group | No. of Male Rats | Dose (mg/Kg) | Dose Volume (mL/kg) | Conc. (mg/mL) | Vehicle | Route |
|---|---|---|---|---|---|---|
| 1 | 3 | 1 | 2 | 0.5 | 50% DMSO/ 50% Saline | IV |
| 2 | 3 | 10 | 2 | 5 | 0.5% MC | PO |
| 3 | 3 | 20 | 2 | 10 | 0.5% MC | PO |

TABLE 4-continued

In vivo Rat PK Study Protocol via Oral (PO) Administration of Compound 118.

| Group | No. of Male Rats | Dose (mg/Kg) | Dose Volume (mL/kg) | Conc. (mg/mL) | Vehicle | Route |
|---|---|---|---|---|---|---|
| 4 | 3 | 40 | 2 | 20 | 0.5% MC | PO |

Rats were dosed once per day for three days. Conc. = concentration; MC = Methylcellulose; PO = oral by gavage.

One the third day, whole blood samples (0.250 mL; K2EDTA anticoagulant) were collected from each animal through a jugular vein catheter. Whole blood samples were collected from all animals pre-dose, and at 0.25, 0.5, 1, 2, 4 after the third day's dose. All blood samples were immediately placed on ice until processing. Whole blood samples were centrifuged at 2200×g for 10 minutes in a refrigerated centrifuge (5±3° C.) to isolate plasma. The plasma samples were transferred to individual polypropylene vials and immediately placed on dry ice before storage at nominally −20±5° C. The plasma samples sometime later were then thawed and extracted and analyzed by high pressure liquid chromatography (HPLC) coupled to Mass Spectrometery (MS). Pharmacokinetic parameters were estimated using WinNonlin® pharmacokinetic software (Version No. 5.2.1) using a non-compartmental approach consistent with the PO route of administration. The rodents were then sacrificed. On Day 3, five hours after dosing, animals were euthanized and whole brain and spine were removed, washed with saline and flash frozen until storage at nominally −70° C. before transfer for concentration analysis. The plasma, brain and spinal tissue samples were analyzed for test article concentration using a Research Grade LC-MS/MS Assay.

The results indicate that Compound 118 exhibited dose linearity in plasma at the 10, 20 and 40 mg/Kg doses as well as compound penetration into the spine and brain in the rat (Table 5). Compound level in the spine ranged from 15-31 ng/mL with the highest level corresponding to the 40 mg/Kg daily oral dose. Compound level in the brain ranged from 30-84 ng/mL with the highest level corresponding to the 40 mg/Kg oral dose (see Table 5).

TABLE 5

Mean PK Results for Oral (PO) Administration of Compound 118 in Male Sprague-Dawley Rats. Compound: 118 Schedule: Single Dose Gender = Male Test Animal = 12 Animal = Rats Strain = Sprague-Dawley Multi-day dosing for 3 days and harvest spine and brain

| Group. | # Rats | Dose | Route | AUC (0-t)[2] (ng * hr/mL) | AUC (0-inf)[2] (ng * hr/mL) | $T_{1/2}$(hr) | Cmax(ng/mL)[3] | Spine[4] (ng/mL) | Brain[4] (ng/mL) |
|---|---|---|---|---|---|---|---|---|---|
| DAY 3 | | | | | | | | | |
| 1 | 3 | 10 mg/kg | PO | 4010 | 12600 | 1.59 | 1450 | 15.6 | 30.2 |
| 2 | 3 | 20 mg/kg | PO | 8820 | 10100 | 1.02 | 3850 | 18.3 | 42.1 |
| 3 | 3 | 40 mg/kg | PO | 15600 | 15800 | 1.01 | 5020 | 31.0 | 84.6 |
| 4 | 3 | 1 mg/kg | IV | 1650 | 1720 | 0.890 | N/A | N/A | N/A |
| DAY 2 | | | | | | | | | |
| 1 | 3 | 10 mg/kg | PO | 4390 | 4480 | 1.24 | 1340 | | |
| 2 | 3 | 20 mg/kg | PO | 4650 | 4730 | 1.28 | 2150 | | |
| 3 | 3 | 40 mg/kg | PO | 12200 | 12200 | 1.02 | 5570 | | |
| 4 | 3 | 1 mg/kg | IV | 1170 | 1170 | 0.936 | N/A | | |
| DAY 1 | | | | | | | | | |
| 1 | 3 | 10 mg/kg | PO | 3770 | 3880 | 1.29 | 1170 | | |
| 2 | 3 | 20 mg/kg | PO | 6410 | 6520 | 1.20 | 2140 | | |
| 3 | 3 | 40 mg/kg | PO | 15600 | 15800 | 1.01 | 5020 | | |
| 4 | 3 | 1 mg/kg | IV | 1810 | 1820 | 0.970 | N/A | | |

[1]The area under the concentration versus time curve for plasma.

[2]The area under the arithmetic mean concentation versus Time curve from time zero to infinity for plasma.

[3]Maximum observed concentration, occurring at Tmax. for plasma.

[4]On Day-3, after dosing, rats were euthanized and spine and brain removed and washed with saline and frozen.

Example 17: Orally Testing Compound 118 and Measuring the Caspase 3 Protein Level in a Rat Model of Spinal Cord Nerve Damage Several laboratory models of spinal cord nerve damage (or spinal cord injury) have been developed and are outlined in by Resnick and coworkers (Annals of Neurosciences, 14, 96-107, 2007). The current model involves the spinal nerve ligation (SNL) injury.

A total of 90 male Sprague Dawley rats (200-225 g) from Envigo (Indianapolis, IN) were used in the study. The 90 rats were assembled into four groups that would be orally dosed (PO) with vehicle, Gabapentin and Compound 118 as follows:

Group 1=Sham+Vehicle, n=20 rats
Group 2=SNL+Vehicle, n=40 rats
Group 3=SNL+Compound 118 (160 mg/Kg), n=20 rats
Group 4=SNL+Gabapentin (100 mg/Kg), n=10 rats Under general anesthesia with continuous inhalation of isoflurane, surgery was performed with aseptic procedures. The skin at the area of the lower lumber and sacral level of the rat was shaved and disinfected with betadine and alcohol. A left longitudinal incision at the level next to the vertebral column was made and the left paraspinal muscles were separated. The transverse process of L6 was removed and nearby connective tissue cleaned to expose L5 and L6 spinal nerves. After the nerves were isolated and clearly visualized, 4-0 silk threads were used to ligate the left L5. The muscles were sutured with 4-0 silk threads and the wound closed by staples. All rats received an analgesic (buprenorphine, 0.05 mg/kg, s.c.) immediately before and 6 hours after surgery. Animals were observed continuously for the level of anesthesia, testing for the animal's reflex response to a tail or paw pinch and closely monitoring the animal's breathing. A heating pad was used to maintain body temperature at 37° C. while the animals recovered from anesthesia. Each rat was monitored until awake and moving freely around the recovery chamber. Animals were then single-housed for the duration of the study.

As a way to measure the behavioral result of the spinal cord injury, the level of mechanical allodynia displayed by the rodents were measured. The mechanical allodynia of the rodents were measured by applying von Frey (VF) filaments (Stoelting, Wood Dale, IL) of ascending bending force to the plantar surface of the hind paws, ipsilateral and contralateral to the surgical manipulation. Filaments ranged from 0.69 to 60 g (0.692, 1.202, 1.479, 2.041, 3.63, 6, 8, 10, 15, 26, and 60). Each filament was applied 3 times to determine withdrawal. A positive response was defined as withdrawal from the von Frey filament. Confirmation of the paw withdrawal threshold (PWT) was tested by assessing the response to the filament above and below the withdrawal response. Rats were brought to the experimental room and allowed to habituate in the room for one hour prior to testing, and acclimated to the observation chambers for 15 minutes prior to taking PWT measurements.

Pre-operative baseline testing: Prior to surgery, all rats were tested using the VF test. Rats that had an ipsilateral PWT of less than 12 g were excluded from the study.

Post-operative testing: Two weeks following surgery, baseline VF responses were taken and animals were balanced and assigned to treatment groups based on their post-operative PWT values. Animals with a VF score over 4.5 g were excluded from the study.

Rats were orally dosed with compound 118 (160 mg/Kg compound 118 in 0.5% methylcellulose, 400 cps solution) or vehicle (0.5% methylcellulose (400 cps) for 5 days. Gabapentin was administered only on von Frey test days (Day 1, 3, and 5). Von Frey PWT values were measured at 60 min following oral administration. FIG. 1 shows the results of the five days of oral dosing. Compound 118 was shown to reduce mechanical allodynia in a statistical manner as compared to vehicle control (FIG. 1). FIG. 1 shows a comparison of ipsilateral paw withdrawal thresholds among post SNL groups. Data are presented as mean±SEM. #$p<0.05$ vs. Sham+Vehicle and *$p<0.05$ vs. SNLsurgery+Vehicle group on same day.

Tissue Collection: After VF test on Day 5, rats were anesthetized by $CO_2$. Blood was collected through cardiac puncture and placed in K2EDTA microcentrifuge tubes and kept on ice. Within 15 minutes, the tubes were centrifuged for 10 mins at 10,000 RPM (~7500×g) in a refrigerated centrifuge. Plasma was extracted, frozen, and stored in a −80° C. freezer. Following blood collection, a blunt-end perfusion needle was inserted into the left ventricle and forwarded toward the ascending aorta. An incision was made in the right atrium and an automated pump was used to perfuse the animal with ice cold PBS. The brain, spinal cord (L4-L6), and dorsal root ganglions (DRGs) (L4, L5, and L6) from both sides (into separate left and right tubes) were collected, flash frozen, and stored in a −80° C. freezer for Caspase 3 analysis.

Figure 2:
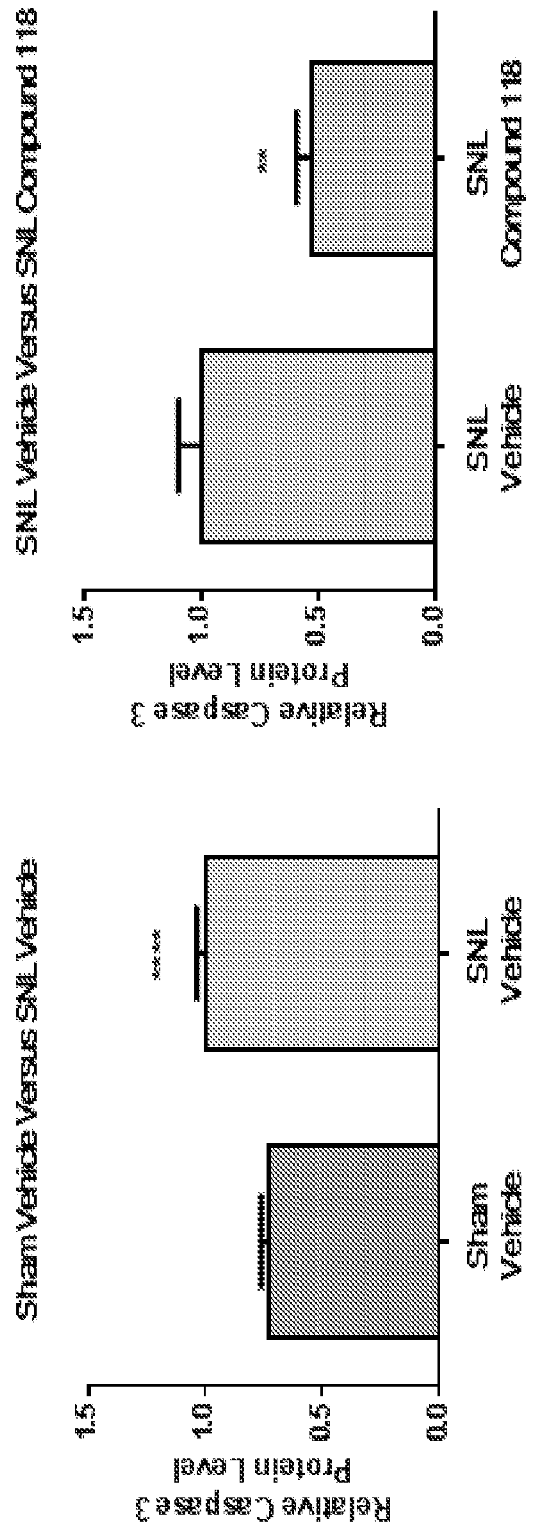
FIG. 2 is a graph of a comparison of caspase 3 protein level measured using western blotting in sham and vehicle (left) and vehicle and compound 118 (right) dosed groups.

The Western blotting method for measuring caspase 3 that is outlined in Example 10 was used. Western blotting was performed on dorsal root ganglion (DRG) of Sham, SNL-vehicle and SNL-Compound 118 groups. FIG. 2 shows the determination of caspase 3 protein level from Left DRG in rats. Comparison between the DRG from Vehicle treated Sham and Vehicle treated SNL rats showed a significant increase of caspase 3 protein level in the Vehicle treated SNL group (FIG. 2, Left). Comparison between the DRG from Vehicle treated SNL rats and Compound 118 treated SNL rats showed a significant decrease of caspase 3 protein in the DRG of SNL rats orally dosed with Compound 118 (FIG. 2, Right). Data is presented as average±SEM. Unpaired t-test was performed: , $p<0.01$; **, $p<0.0001$.

It was confirmed that after spinal injury there was an increase in mechanical allodynia (FIG. 1), which corresponds to an elevation in caspase-3 protein levels (FIG. 2) in the dorsal root ganglion as compared to the sham control. Once per day oral dosing with Compound 118 produced a statistically significant decrease in mechanical allodynia (FIG. 1) and a decrease in the caspase-3 protein levels as compared to the vehicle group (FIG. 2). The results of this study demonstrate that oral dosing of Compound 118, can ameliorate nerve damage via regulating apoptotic pathways, and specifically through reduction of caspase-3.

Example 18: Orally Testing Compound 5 and Measuring the Caspase 3 Protein Level in a Streptozotocin (STZ) Induced Rat Model of Neurodegeneration When diabetes is not controlled, too much sugar remains in the blood. Over time, this can damage organs and nerves, including the brain and spine. Scientists are finding strong evidence of a link between Type 2 diabetes and Alzheimer's disease (de La Monte, and coworkers, Journal of Diabetes Science and Technology, 2(6), 1101-1113 (2008)). Streptozotocin (STZ)-induced rodent model is one of the classic models for inducing type 2 diabetes in rodents. The hyperglycemic conditions induced in the STZ rodent model has been observed to cause elevation in caspase 3 and neuronal cell death (Vincent, A. M. and coworkers, Ann. N.Y. Acad. Sci., 959, 368-383 (2002)).

Male Wistar rats (300-350 g) at the beginning of the experiment were used. A single dose (65 mg/kg, i.p.) of Streptozotocin (STZ) with 230 mg/kg (i.p) of nicotinamide were used for induction of diabetes in rats. The STZ was freshly dissolved in citrate buffer. Age matched control rats received the equal volume of the citrate buffer only. Forty days after injection of either STZ or citrate buffer, the rats were tested for diabetes mellitus (DM) using a drop of blood from the tail vein. The estimation of blood glucose level was made using OneTouch Select® Glucometer (LifeScan, Inc., USA). Rats with plasma glucose level>8 mmol/1 (145 mg/dl) were considered as diabetic. Following the diagnosis of DM, age matched healthy control and STZ-induced diabetic rats were divided randomly into four groups each containing six rats. Glucose level was estimated on weekly basis during the experiment.

Experimental design and drug treatment: Six weeks after the diabetic induction age matched healthy control and STZ-induced diabetic rats were divided randomly into four groups each containing six rats: naïve rats, vehicle (0.5% methylcellulose) treated DM group, 70 mg/kg (in 0.5% methylcellulose) Compound 5-treated DM group, 140 mg/kg (in 0.5% methylcellulose) Compound 5-treated DM group.

Behavioral testing: Tactile allodynia. Rats were placed in a plastic cage with a metal grid bottom, which allows full access to the paws. The paw withdrawal thresholds were determined. Paws were touched with one of a series of 8 von Frey hairs with logarithmically incremental stiffness (0.692, 1.202, 2.041, 3.630, 5.495, 8.511, 15.136, 28.840 g). The testing was initiated with the 3.630 g hair. The psychophysical 50% threshold was then calculated.

Immunohistochemistry: Sections from the biopsy specimens were formalin-fixed and paraffin-embedded. For immunohistochemistry (IHC) examination, slides from the spinal cord and sciatic nervous were evaluated for caspase-3. Serial 3-5-μm thick sections were cut from paraffin embedded tissue blocks. For subsequent IHC staining glass slices were exposed to hot unmasking fluidized citrate buffer pH 6.0 for 15-18 min. After cooling, the glass with the slice was transferred into phosphate-buffered saline (PBS) pH 7.4. The sections were deparaffinized and then rehydrated in alcohol to tris-buffered saline. Endogenous peroxidase activity was blocked using 3% hydrogen peroxide followed by a protein block with 5% goat serum. Affinity purified monoclonal $IgG_1$, Caspase-3 p11 (C-6) antibodies (sc-27159; Santa Cruz BioTechnology Inc., Dallas, TX, USA) were used as the primary antibody and applied at a 1:50 dilution 100 μl/glass for 30 min at room temperature. Labeled streptavidinbiotin (LSAB) was used for the detection system with diaminobenzidine tetrahydrochloride (DAB) as the chromogen. All sections were washed in PBS, examined under Olympus BX51 microscope and photographed with Carl Zeiss Axio Scope A1 light microscope with digital camera AxioCamlCc 1 at ×100, ×200, ×400 and ×1000 magnifications. Measurement of the optical density was carried out with VideoTest Size ver. 5.0. Sixty animals (4 per group) and three sections from each animal were used for quantitative immunohistochemistry (12 measuring per each group).

Data analysis: The results are presented as mean±SEM. In chronic pain experiment, four rats were excluded from the statistical analysis because the paw withdrawal threshold was >8 g (criterion taken from the study. Paw withdrawal threshold data were subjected to analysis of variance (ANOVA, General Linear Model procedure) with Dunnett's post hoc test was applied for between-group pair wise comparisons. Effects of Compound 5 on immunohistochemistry parameters were analyzed by one-way ANOVA (factors: Compound 5 treatment) followed by the Dunnett's test. Data were analyzed using SAS-STAT (SAS v.9.4, SAS Institute Inc., Cary, NC, USA). Data were considered significant at $P<0.05$.

Figure 3:
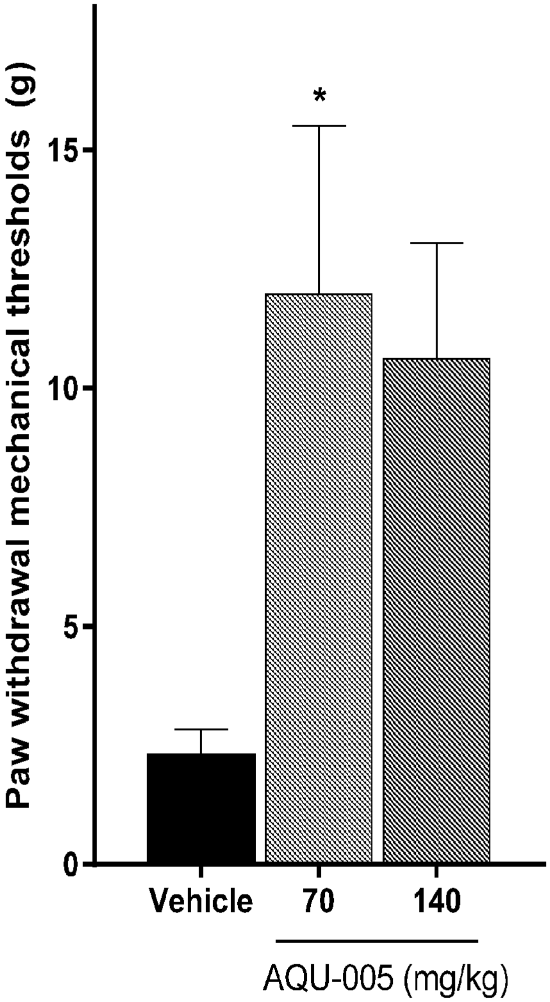
FIG. 3 is a graph of the effect of Compound 5 on tactile allodynia.

Results—Effects of Compound 5 on tactile allodynia in diabetic rats: Compound 5 effects on tactile allodynia in diabetic rats are shown in FIG. 3. As represented in FIG. 3, "Vehicle"—vehicle-treated DM group (14 days treatment), n=10. "70"—70 mg/kg Compound-5-treated DM group (14 days treatment), n=12; "140"—140 mg/kg Compound-5-treated DM-group (14 days treatment), n=10; Data presented as mean±SEM. *–$p<0.05$ vs. Vehicle-Control group; by one-way ANOVA with followed by Dunnett's test. On the $40^{th}$ day of DM onset (before Compound 5 treatment) tactile reactivity significantly increased in all experimental DM group compared to naïve group. After 14 days of treatment with Compound 5 the threshold of the nociceptive response significantly decreased. Post hoc analysis confirmed the effect of Compound #5 on tactile allodynia at a dose of 70 mg/kg. Compound 5 at a dose 140 mg/kg showed a tendency to the analgesic effect.

Effects of Compound 5 on blood glucose concentration and glycosylated hemoglobin ($HbA_{1C}$): Blood glucose concentration was increased ~2 to 3-fold in diabetic rats compared with naïve group. Compound #5 administration had no significant effects on glucose concentration. At the $14^{th}$ day of the treatment period, the $HbA_{1c}$ levels were higher in the DM group than in the naïve group. The $HbA_{1c}$ level of the DM rats treated with Compound #5 during 2 weeks was not significantly changed compared with that of the untreated DM rats.

Figure 4:
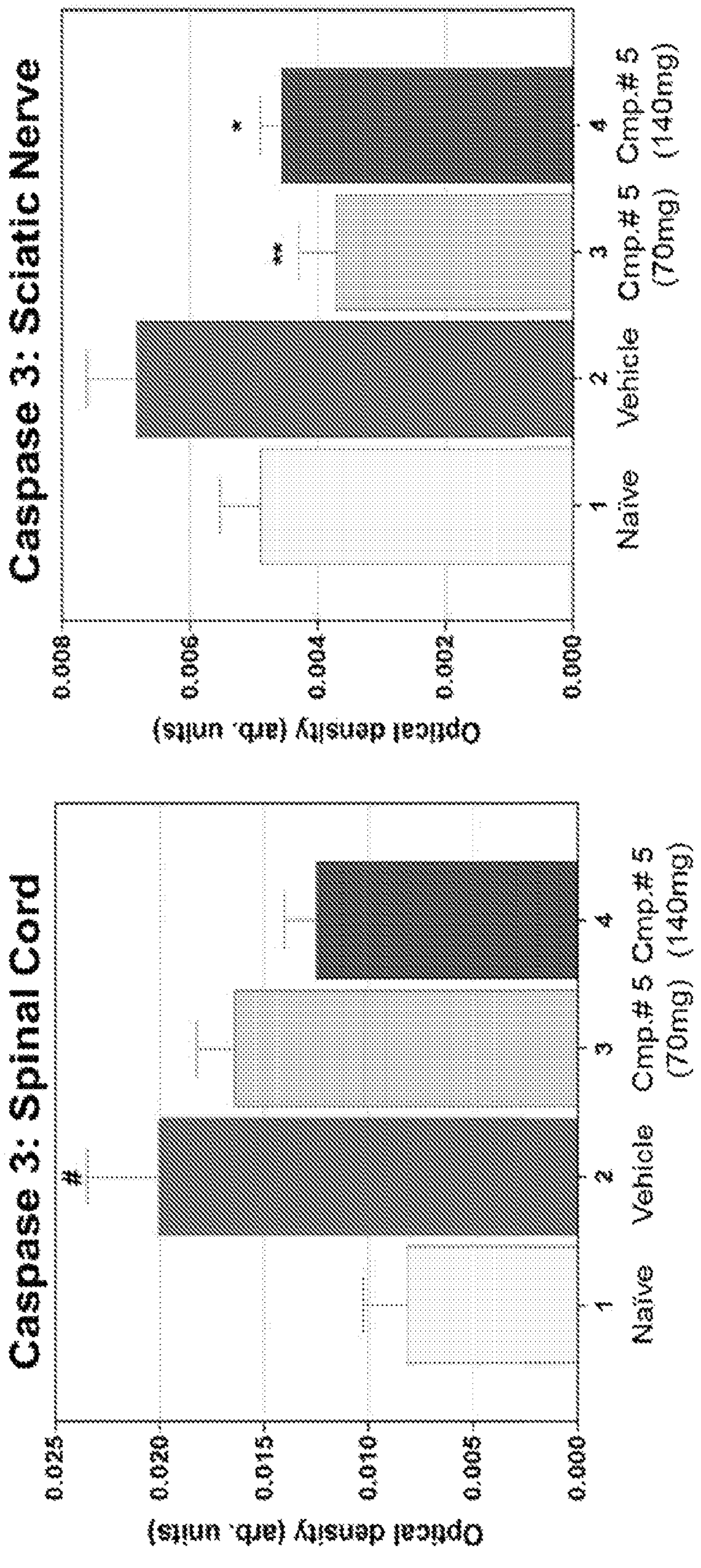
FIG. 4 is a graph of optical density of caspase-3 in spinal cord and sciatic nerves.

FIG. 4 shows optical density of caspase-3 in spinal cord and sciatic nerve of naive (1), vehicle-treated DM group (2), 70 mg/kg Compound-5-treated DM group (3) and 140 mg/kg Compound-5-treated DM group (4) rats. Data represent mean±S.E.M. #–$p<0.05$, vs. naïve group; *–$p<0.05$, **–$p<0.01$, vs. Vehicle-Control group; By one-way ANOVA followed by Dunnett's test.

Effects of Compound 5 on expression of caspase 3 in diabetic rat: One-way ANOVA showed a significant effect of Compound 5 treatment on the caspase-3 protein level (FIG. 4). Post-hoc analysis confirmed significant reduction of the expression of caspase-3 after Compound 5 treatment in both doses compared to vehicle-treated DM group in sciatic nerve (FIG. 4). In spinal cord the treated compound 5 group showed a statistically significant change compared to vehicle group (FIG. 4).

The results of this study demonstrate that oral dosing of Compound 5, can ameliorate nerve damage caused by DM via regulating apoptotic pathways, and specifically through reduction of caspase-3.

Example 19: In-Vivo Oral Pharmacokinetics (PK) Testing of Compound 118 in SOD-1 Mice It is important if one is observing biochemical effects in the spine that one is able to show clear evidence that the compound being tested is in fact able to exhibit good oral bioavailability in both plasma and target tissues (spinal cord). The present example orally doses compound 118 once per day (SID) or twice per day (BID) for three days to a series of mice that have overexpression for the protein copper-zinc superoxide dismutase 1. Compound 118 was orally dosed in SOD-1-G93A (SOD-1) mice in a PK study. In summary, SOD-1 mice (At P100±4 days of age) received twice daily (BID) or once daily (SID) oral administration of 200 mg/Kg Compound 118 (as an aqueous suspension in 0.5% methylcellulose) for 3 days (Table 6). Plasma was collected from the tail vein at baseline (pre-dose), 15 min, 30 min, 1 h, 2 h, 4 h post-last PO dose on the third day. One animal from each group was euthanized 2 hrs. post dose on the third day of dosing where plasma, spinal cord, and brain tissue was collected post-mortem. The remaining 3 animals per group was euthanized six hours after the final dose on the third day, plasma, spinal cord, and brain tissue was then collected post-mortem. The results showed that AQU-118 exhibited good bioavailability in plasma. AQU-118 was detected in the spinal cord with concentration levels that were found to range between 200-400 ng of AQU-118/gram spinal tissue at T=2 hour from last dose. There was a significant difference in clearance of Compound 118 within plasma between male and female SOD-1 mice. AQU-118 was observed to have an area under the curve (AUC) that was 3-4 times higher in Female SOD-1 mice than for male SOD-1 mice (Table 7). The results of this study show that Compound 118 has good oral bioavailability in SOD1 mice. Given the sex difference in clearance, it will be necessary to increase the amount that male SOD-1 mice are dosed compared to females SOD-1 mice in order maintain parity in exposure between the sexes.

one variety of fALS has been inserted into transgenic mice the SOD-1-G93A (SOD-1) strain. These mice develop a phenotype that is similar to human ALS, with progressive loss of motor neurons, generalized muscle weakness and atrophy, and eventual death. This model has been used widely and productively to screen potential new treatments for human ALS. For example, the one currently marketed drug for ALS, riluzole, increases mean survival in mutant mice by 10-14 days, equivalent to about a 3 month increase in survival in human ALS patients. There are several factors when running the SOD-1 mouse model of ALS. These factors are as follows (Leitner, M. et al. Working with ALS mice, Manual prepared by the Jackson Laboratory and the Prize4 Life foundation, pages 1-21).

1) Gender: It is necessary to use equal numbers of males and females in all cohorts: This model shows clear gender differences in survival, with female animals living on average 4-7 days longer than males.
2) Litter: It is necessary to balance littermates across experimental cohorts. This model shows that litter mates have similar age of onset of disease and death.
3) Transgene copy number: It is necessary to measure the transgene copy number for all animals used in the model study to make sure that they all have similar copy numbers. Over time the mutant SOD-1 transgene undergoes a background level of copy loss resulting in extension of lifespan.

TABLE 6

| Treatment Groups | | | | | | | | |
|---|---|---|---|---|---|---|---|---|
| Group | N | Sex | Substance | Dose (mg/kg) | Concentration (mg/ml) | Volume (ml/kg) | Route | Regimen |
| 1 | 4 | Male | Compound 118 | 200 | 20 | 10 mL/kg | PO | BID |
| 2 | 4 | Male | Compound 118 | 200 | 20 | | | SID |
| 3 | 4 | Female | Compound 118 | 200 | 20 | | | BID |
| 4 | 4 | Female | Compound 118 | 200 | 20 | | | SID |

TABLE 7

| Mean PK Results for Oral (PO) Administration (200 g/Kg) of Compound 118 in Male & Female SOD-1 Mice at P100 (±4 days of age) | | | | |
|---|---|---|---|---|
| Group | SEX | Frequency | Average Cmax (ng/mL) | Average AUC (hr * ng/mL) |
| 3 | F | BID | 110,975.00 | 394,025.00 |
| 4 | F | SID | 95,975.00 | 341,946.88 |
| 1 | M | BID | 39,150.00 | 114,705.00 |
| 2 | M | SID | 44,475.00 | 121,445.00 |

Example 20: Oral (PO) Testing of Compound 118 in the SOD1 Mouse Model of Amyotrophic Lateral Sclerosis (ALS)

Background of ALS model: ALS is manifest by progressive death of motor neurons in the brain and spinal cord. Among families with familial ALS (fALS), several mutant genes have been identified. The first and most common of these to be discovered is a mutation in the gene encoding for the free radical scavenging enzyme superoxide dismutase-1. The mutant human superoxide dismutase-1 gene causing 4) Exclusion Criteria: Any animal which fails to undergo the predicted disease progression should be systematically excluded from treatment analysis and the reason for exclusion should be recorded and reported
5) Onset/Timing of Treatment: The combination of peak body weight followed by decreasing neurological score is a reasonable measure to determine disease onset in the ALS SOD-1 mouse model. It is well documented that SOD-1 mice display disease on-set at peak weight which is around 100 (±4 days of age) days from birth (P100) (Olivan, S., et al., Experimental Animal, 64(2), 147-153, (2015)). This includes severe muscle weakness, hind limb tremors and a 50% survival at 128.9+/−9.1 days (wild type mice exhibit a 50% survival at 157.1+/−9.3 days)
6) Primary endpoint is the inability of an animal to right itself within 15-30 seconds if laid on either side.

Secondary endpoint is time on Rotarod. In the test, a rodent is placed on a horizontally oriented, rotating cylinder (rod) suspended above a cage floor, which is low enough not to injure the animal, but high enough to induce avoidance of fall. Rodents naturally try to stay on the rotating cylinder, or rotarod, and avoid falling to the ground. The length of time that a given animal stays on this rotating rod is a measure of their balance, coordination, physical condition, and motor-planning. The speed of the rotarod is mechanically driven, and may either be held constant, or accelerated.

Experimental outline: The SOD-1-G93A (SOD-1) mouse groups was both gender balanced and litter matched in order to remove as much bias as possible. In addition to using SOD1-G93A mice groups, normal non-SOD-1 (Wild Type, WT) mice were also used as a way to compare both species' survivability. A three-ways mixed model ANOVA was performed on rotarod & body weight data with treatment and gender as independent factors and age dependent factors. The timetable for these studies was as follows: Three groups of SOD-1 mice transgenic mice (16 male and 16 females per group) and one group of Wild Type mice (16 male and 16 female) arrived from Jackson Labs (Table 8). Baseline Rotarod testing began at P100 (±4 days of age) and then once a week after that. Compound 118 or vehicle was administered either BID or SID right after base-line rotarod measurement at P100 (±4 days of age) which corresponded to the first appearance of symptoms of neuromuscular deficit. Male SOD-1 mice were dosed at a higher level than females due to the fact that they exhibited higher levels of clearance observed in Example 19 (Table 8). Primary endpoint was the inability of the rodent to right itself (i.e., righting reflex) within 15-30 seconds if laid on the either side. Secondary endpoint is the length of time on rotarod and improvement in neurological score as determined as follows:

Neurological Scores: Stage 0: No symptoms; Stage 1: Body tremor, leg tremor, spiked fur, slowed locomotor behavior. Mouse will look generally un-groomed and slightly weak. Normal righting reflex; Stage 2: Hind limb dragging, Paw Curling, Ataxia, slower righting reflex, hind limb splay, stage 1 symptoms; Stage 3: Hind limb paralysis, hair loss, slightly emaciated, lack of rearing ability, delayed righting reflex, stage 2 symptoms; Stage 4: unable to walk and lying on side, Hunched back, Paralysis of 2 or more limbs, emaciated, delayed righting reflex, stage 3 symptoms.

TABLE 8

Protocol for ALS study using SOD-1 male and female mice.

| Group | #Mice Male/Female | Strain | Dose (mg/kg)/Frequency | Compound |
|---|---|---|---|---|
| 1 | 16M/16F | WT[1] | SID[2] | Vehicle[3] |
| 2 | 8M/8F | SOD1 | SID[2] | Vehicle[3] |
| 3 | 8F/8M | SOD1 | SID[2] | Vehicle[3] |
| 4 | 16F | SOD1 | 200 SID[2] | Compound 118[4] |
| 5 | 16M | SOD1 | 350 SID[2] | Compound 118[4] |
| 6 | 16F | SOD1 | 200 BID[2] | Compound 118[4] |
| 7 | 16M | SOD1 | 350 BID[2] | Compound 118[4] |

[1]WT = Wild Type.
[2]SID = Once per day, BID = twice per day
[3]Vehicle consisting of 0.5% methylcellulose and given via oral gavage
[4]Compound is suspended in 0.5% methylcellulose & given via oral gavage.

Example 21: Oral (PO) Testing of Compound 5, 118 or 82 in a Model of Duchenne Muscular Dystrophy (DMD)

Background: DMD is an inherited X-linked disease that results in the loss of dystrophin, a protein involved in maintaining the integrity of muscle. C57BL/10ScSn-Dmdmdx/J mice (common name mdx) have a loss-of-function mutation in the dystrophin gene that underlies progressive muscle degeneration starting about three weeks of age. In this model the mdx mice show reduced grip strength (both forelimb and hind limb) at four weeks of age compared with control mice. At eight weeks, the mdx forelimb strength decreases while the hind limbs show normal strength. Such findings reflect the progression of the acute phase of muscle necrosis in the young mdx mice. Muscle atrophy, inflammation and fibrosis are present in the mdx mice at eight weeks of age. The read-outs for this model are grip strength measurement, locomotive testing, rotarod and histopathology.

Procedure: To perform the model an equal number of males (12) and females (12) mdx mice can be obtained from Jackson Laboratories (Bar Harbor, ME, USA) and used in each group. Litters of 3-week-old animals can be treated daily by oral gavage for 7 weeks and analyzed via locomotive testing, grip strength and rotarod once per week for 10 weeks of age. Animals could then receive daily oral gavage administration of vehicle (0.5% methylcellulose), Compound 5, 118 or 82 (20 mg/kg/d, 40 mg/kg/d in methylcellulose 0.5%) or positive control (Table 9)

TABLE 9

Protocol for DMD study using mdx male and female mice.

| Group | #Mice Male/Female | Route | Dose[1] (mg/kg) | Compound |
|---|---|---|---|---|
| 1 | 12/12 | p.o. | NA[2] | Vehicle[3] |
| 2 | 12/12 | p.o. | 20 | 118 |
| 3 | 12/12 | p.o. | 40 | 118 |
| 4 | 12/12 | p.o. | 20 | 5 |
| 5 | 12/12 | p.o. | 40 | 5 |
| 6 | 12/12 | p.o. | 20 | 82 |
| 7 | 12/12 | p.o. | 40 | 82 |
| 8 | 12/12 | p.o. | 5 | Prednisolone[4] |

[1]Once per day dosing via gastric gavage.
[2]NA not applicable
[3]0.5% methyl cellulose.
[4]Positive control

Example 22: Intrathecal (i.t.) Administration of Compound 118 and 5 in the Spinal Nerve Ligation (SNL) Mouse Model This example is presented to demonstrate dosing of the compound of the present disclosure via i.t. administration via injection. Following preoperative baseline (Day −2) paw threshold measurement, FVB male mice were subjected to spinal nerve ligation (SNL) injury (Day −1). The next day (Day 0) after SNL surgery, the animals were tested for post-operative baseline threshold measurements for mechanical allodynia; and the animals were then randomly assigned to one of 3 treatment groups (see Table 10). Over the course of the study, paw withdrawal threshold of these animals was measured in response to mechanical stimulation using the von Frey Monofilament Test.

The compounds of the present disclosure were delivered into the cerebral spinal fluid (CSF) space around lumbosacral spinal cord via intrathecal (i.t.) administration, with the idea of the compounds reaching the dorsal root ganglion (DRF), spinal cord, and spinal CSF. Intrathecal administration could then target not only spinal cord cells but also DRG cells. Each intrathecal (i.t.) injection was carried out according to the technique of Hylden and Wilcox (Hylden J L, Wilcox G L. Eur. J Pharmacol., 67, (1980), 313-6) 5.2 mg of each of compounds 5 and 118 were first dissolved in 140 microliters of DMSO and then put into 1260 microliters of 0.5% hydroxypropyl cellulose (HPC) in water to make a final solution composed of compounds in 10% DMSO-0.5% hydroxypropyl cellulose. 10 microliters of the mixture was injected into the intrathecal space of male FVB mice (weighing 22-25 grams each and obtained from the Jackson Laboratories, Bar Harbor, ME), by lumbar puncture in a volume of 10 μl/mouse using a Hamilton micro syringe via a 30 gauge needle inserted between lumbar vertebrae 5 and 6. In brief, each animal was held firmly by the pelvic girdle in one hand, while the needle was inserted into the tissue on the right side of the L5 or L6 spinous process. The needle was moved forward and slipped into the groove between the spinous process and transverse process and gently moved forward to the intervertebral space at ~10° angle. As the needle was inserted (~0.5 cm) within the vertebral column a tail flick was evident, and the solution was then injected. Table 10 summarizes the various treatment groups and frequency of administration.

TABLE 10

Animal i.t. Treatment Groups & Compounds Tested

| Treatment | # of Mice | Dose | Route of Administration And Frequency |
|---|---|---|---|
| Vehicle | 8 | Group 1, 10 μl/mouse | i.t., daily injections, from day 1-6, starting day 1 |
| Compound 5 | 4 | Group 2, 10 μl/mouse | i.t., daily injections, from day 1-6, starting day 1 |
| Compound 118 | 5 | Group 3, 10 μl/mouse | i.t., daily injections, from day 1-6, starting day 1 |

*Vehicle = 10% DMSO, 0.5% hydroxypropyl cellulose in water

Tactile Allodynia Test. Mechanical allodynia was measured using the calibrated von Frey filaments (Semmes-Weinstein monofilaments; Stoelting, Wood Dale, IL, U.S.A.). The plantar surface of the left injured paw of each animal was tested as described by Chaplin et al. (Journal of Neuroscience Methods, 53, (1994), 55-63). The Fifty percent paw withdrawal threshold response was determined by sequentially increasing or decreasing the stimulus strength according to the "up-down method" of Dixon (Annual Review Pharmacology Toxicology, 20, (1980), 441-462). For mice, eight von Frey filaments were used, with approximately equal logarithmic incremental bending forces (von Frey number: 1.65, 2.36, 2.44, 2.83, 3.22, 3.61, 3.84, 4.08, and 4.17; equivalent to 0.005, 0.02, 0.03, 0.07, 0.17, 0.41, 0.69, 1.20, and 1.48 g force, respectively).

Example 23: Testing of Compound 118 in the TDP-43 *Drosophila* Model of ALS with Larval Turning Read-Out ALS is inherited in 5 to 10 percent of cases (familial form), while the other cases appear to occur randomly (sporadic form). TAR DNA-binding Protein 43 (TDP-43) has been identified as the major pathological protein that is produced in the degenerating motor neurons in sporadic ALS. One ALS animal model used to test the effectiveness of a drug is the *Drosophila* model of ALS based on overexpression of TDP-43 and has been described in detail by Zarnescu and coworkers (Human Molecular Genetics, 24(6), 1741-1754, 2015).

Procedure: UAS TDP-43 male *Drosophila* flies were crossed with D42-Gal4 female virgins on fly food containing either DMSO or 1% Compound 118 in dimethyl sulfoxide (DMSO). For DMSO controls, the same volume of DMSO as the corresponding Compound 118 concentration was added. Bromophenol blue was added to a final concentration of around 0.02% to ensure homogeneity. Crosses were made on drug food with three female virgins and two males in each vial and were maintained at 25° C. unless noted. The parents were discarded after 5-7 days and then the vials were screened for adult progeny with straight wings from Day 14 to Day 25. All adults were screened for TDP-43 expression by visualizing the YFP tag. Total number of pupae was counted on Day 25. Percent survival was calculated using the formula (total number of straight-winged adults/total number of pupae)×100. All experiments were performed in triplicate. Read-outs include larval turning assay and pupil lethality screen.

Figure 5:
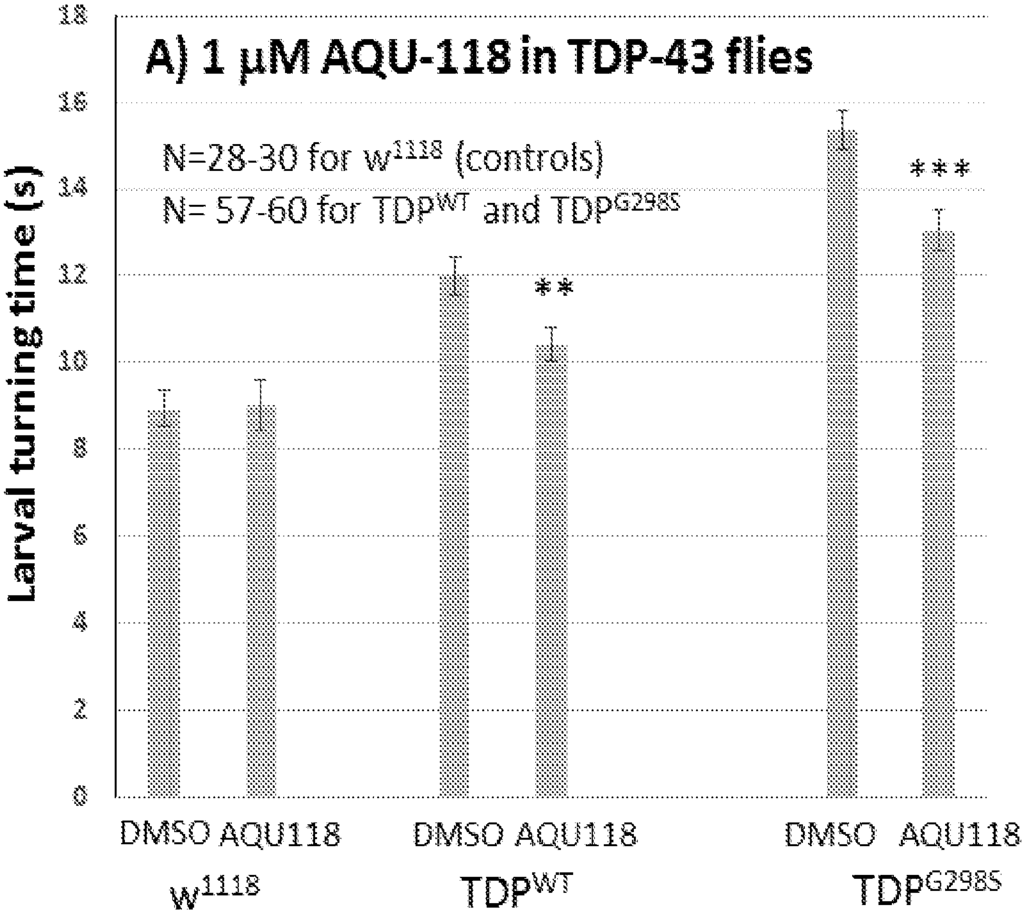
FIG. 5 is a graph of a TDP-43 *Drosophila* ALS model with larval turning read-out.

FIG. 5 shows a TDP-43 *Drosophila* ALS model with Larval Turning Read-out. Data shows that Compound 118 (represented as AQU-118) at 1 microMolar is able to mitigate locomotive defects via larval turning times caused by separate TDP-43 overexpression in *Drosophila* motor neurons. $TDP^{WT}$=Wild-type TDP-43, $TDP^{G298S}$=Diseases associated G298S mutant expressed in motor neurons. p<0.01, p<0.01, ***p<0.001 as compared to DMSO as vehicle.

Figure 6:
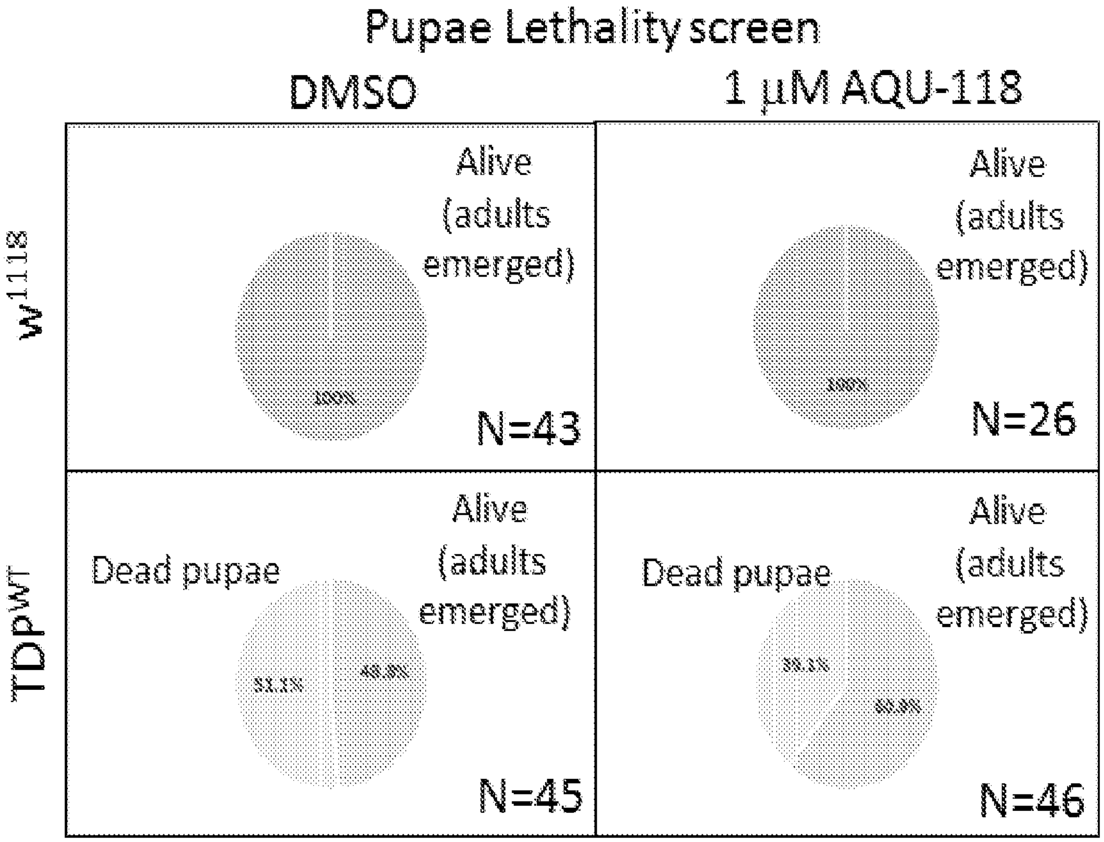
FIG. 6 is a chart of a TDP-43 Pupal Lethality Screen.

FIG. 6 shows a TDP-43 Pupal Lethality Screen: This assay measures the effect of Compound 118 (represented as AQU-118) on the viability of the emerging TDP overexpressed pupae. Compound 118 (represented as AQU-118) caused a decrease in lethality from 51% (bottom left) to 39% (bottom right). In this screen the number of adult TDP-43 overexpressed flies that emerge from their pupae stage is compared to w1118 controls. Larvae were raised on either DMSO or Compound 118 at 1 microMolar. N=number of pupae counted. Alive=empty pupal cases, adults have emerged. Dead pupae=pupae have not emerged, measure of lethality.

The results show that Compound 118 (represented as AQU-118 in FIGS. 5 and 6) at 1 microMolar is able to mitigate locomotive defects via larval turning compared to vehicle control (FIG. 5) and found to decrease the lethality of TDP-43 overexpressed flies that emerge from their pupae (FIG. 6).

The results of this study demonstrate that dosing of Compound 118, can ameliorate motor neuron decline & death associated with overexpression of TDP as found in ALS.

Example 24: Testing of Compound 118 in the SOD-1 *Drosophila* Model of ALS with Larval Turning Read-Out Of the familial form of ALS, about 20 percent result from a defect in the gene that encodes the enzyme copper-zinc superoxide dismutase 1. Another ALS animal model used to test the effectiveness of a drug is the *Drosophila* model of ALS based on overexpression of the enzyme copper-zinc superoxide dismutase 1 and has been described in detail by Zarnescu and coworkers (Human Molecular Genetics, 24(6), 1741-1754, 2015).

Procedure: Following the method of Zarnescu and coworkers (Human Molecular Genetics, 24(6), 1741-1754, 2015). UAS SOD-1 male *Drosophila* flies were crossed with D42-Gal4 female virgins on fly food containing either DMSO or 1% Compound 118 in dimethyl sulfoxide (DMSO). For DMSO controls, the same volume of DMSO as the corresponding Compound 118 concentration was added. Bromophenol blue was added to a final concentration of around 0.02% to ensure homogeneity. Crosses were made on drug food with three female virgins and two males in each vial and were maintained at 25° C. unless noted. The parents were discarded after 5-7 days and then the vials were screened for adult progeny with straight wings from Day 14 to Day 25. All adults were screened for SOD-1 expression. Read-outs involved the larval turning assay.

Figure 7:
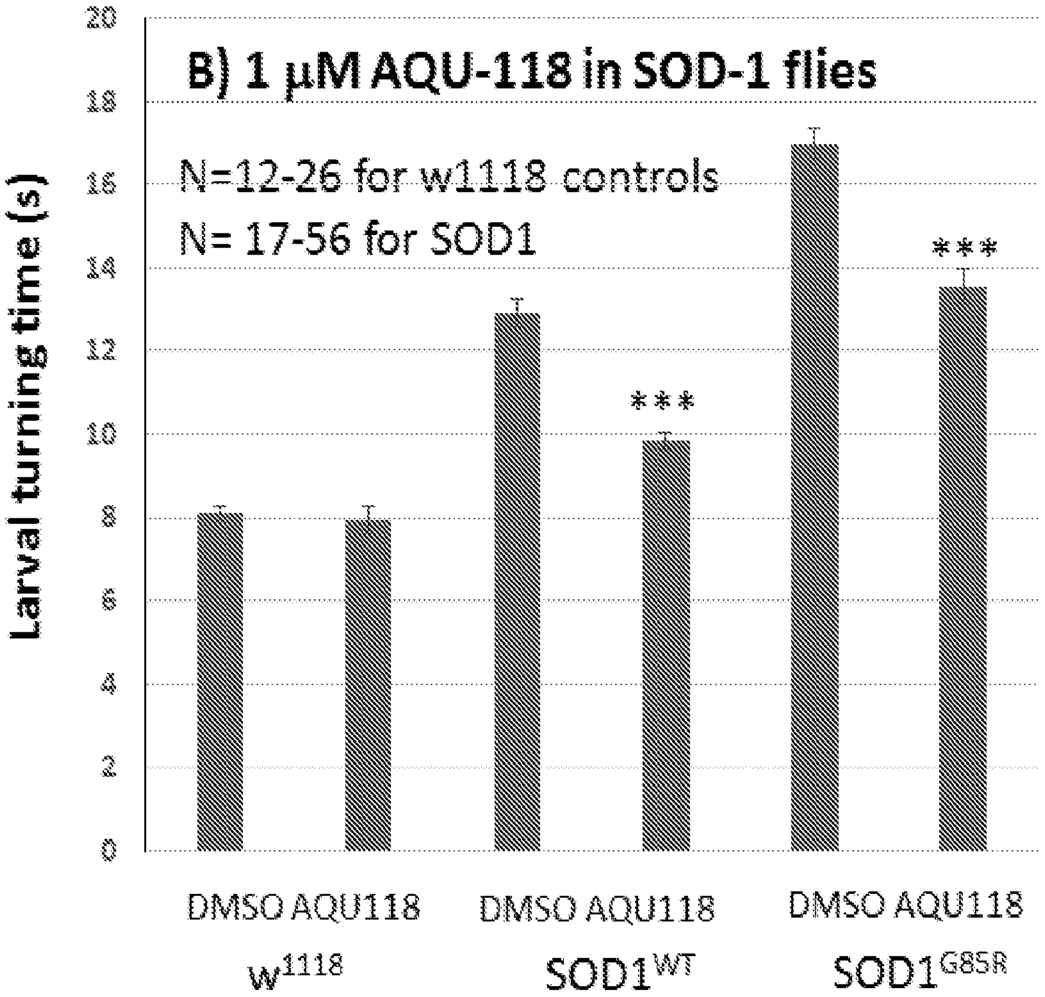
FIG. 7 is a graph of a SOD-1 *Drosophila* ALS model with larval turning read-out.

FIG. 7 shows a SOD-1 *Drosophila* ALS model with Larval Turning Read-out. Data shows that Compound 118 (represented as AQU-118) at 1 microMolar is able to mitigate locomotive defects via larval turning times caused by separate SOD-1 overexpression in *Drosophila* motor neurons. SOD-$1^{wt}$=Wild-type, $SOD1^{G85R}$=Diseases associated G85R mutant expressed in motor neurons. p<0.01, p<0.01, ***p<0.001 as compared to DMSO vehicle.

The results show that Compound 118 (represented as AQU-118 in FIG. 7) at 1 microMolar is able to mitigate locomotive defects via larval turning compared to vehicle control (FIG. 7).

The results of this study demonstrate that dosing of Compound 118, can ameliorate motor neuron decline & death associated with overexpression of SOD1 as found in ALS.

Example 25: Testing of Compound 118, 5 or 82 in a Stressed Induced Rat Model of Inflammatory Bowel Disease (IBD)

Use of chronic stress is a well established method for inducing IBD-like symptoms in the rat. In particular, it has been established that water avoidance stress (WAS) is one of the most effective psychological stressors to induce IBD symptoms. One could use the method of Fourie and coworkers (Gut Microbes, Volume 8, No. 1, pages 33-45, (2017) to measure the effect of oral dosing of Compound 118, 5 or 82 in a stressed induced model of IBD. In this model, following a slightly modified method of Fourie and coworkers (Gut Microbes, Volume 8, No. 1, pages 33-45, (2017), 26 male Sprague Dawley rats could be placed on a glass platform in the center of a tank filled with water 1 cm below the height of the platform. The rodents could then be allowed to stay on the platform for 1 hour at the same time each day for 15 consecutive days. As a control 13 other rodents could then be treated in the same way but in a tank without water for the same amount of time each day. On the $11^{th}$ day the WAS rodents could then be divided into two groups of 13 each. One group could then be orally dosed with Compound 118, 5 or 82 and the other group dosed with a vehicle control (0.5% aqueous methylcellulose) via oral gavage. Dosing would then continue daily for 5 days. At the end of the $15^{th}$ days of WAS and after the last day of oral dosing, the colon-mucosa microbiome could then be characterized and then compared between the three groups (drug, vehicle control and sham control). In addition, the levels of caspase 3 could then be measured by western blot or ELISA of the colon tissue.

Example 26: Example Formulations of Compounds 118, 5 or 82 for Intravenous Dosing For intravenous bolus administration possible carriers or vehicles are saline or up to 5% dextrose or methylcellulose. Acceptable pH ranges for compounds of the present disclosure are 4 to 8 and for unbuffered vehicles 3 to 9. The buffer strength should be kept below 10 millimolar. If solubility is an issue the use of co-solvents such as ethanol, propylene glycol or polyethylene glycol 400 could be used. For intravenous infusion since the volume of the infusion is likely to be greater than used in a single bolus injection then the pH and tonicity should be restricted to a range much closer to physiological values (pH 7 to 8, buffer of 1-10 millimolar in concentration). Since the dissociation constant (Ka) for Compounds 118, 5 & 82 is around 3.4 a buffer needs to be used that can maintain the compound within above that pH in order to maintain a dissociated state. Table 11 shows a list of some comm pharmaceutical buffers (Lee, Y. C and coworkers, International Journal of Pharmaceutics 253, pages 111-119 (2003)), that could be used to modify the final pH in order to improve solubility of the acid.

TABLE 11

Common buffers for maintaining compounds in solution.

| Buffering agents | pKa | pH range |
|---|---|---|
| Tartaric acid | 2.9, 4.2 | 2.5-4 |
| Citric acid | 3.1, 4.8, 6.4 | 3-7 |
| Acetic acid | 4.75 | 4-6 |
| Sodium bicarbonate | 6.3, 10.3 | 4-9 |
| Sodium phosphate | 2.2, 7.2, 12.4 | 6-8 |

Precipitation upon dosing remains significant challenge for solution formulations, this risk can be evaluated by using a series of serial dilutions of the dosing solution using phosphate buffer (pH 7.4, $Na_2HPO4$-NaH2PO4 buffer) with a concentration of 0.067M which would be similar to whole blood.

As was mentioned earlier one can use a co-solvent as part of the vehicle. In Table 12 are a list of possible cosolvents or surfactants that can be used to assist in solubilizing the compounds of present disclosure.

TABLE 12

Common co-solvents or surfactants for maintaining compounds in solution.

| | Cosolvent or surfactant | Range of concentration |
|---|---|---|
| Cosolvent | N-methylpyrrolidone (NMP) | 10-20% (oral, i.v.) |
| | dimethyl sulfoxide (DMSO) | 10-20% (oral or i.v.) |
| | N,N-dimethylacetamide (DMA) | 10-30% (i.v.) |
| | Ethanol | 10% (oral, i.v.) |
| | propylene glycol (PG) | 30-60% (oral, i.v.) |
| | polyethylene glycol 400 | 40-100% (oral, i.v.) |
| | diethylene glycol monoethyl ether | 30% (oral) |
| Surfactant | polyoxyethylene-sorbitan-monooleate (TWEEN 80) | 80 5-10% (oral, i.v.) |
| | polyoxy1-35 castor oil (Cremophor EL) | 5-10% (oral, i.v.) |
| | polyoxyl 40 hydrogenated castor oil (Cremophor RH40) | 5-10% (oral, i.v.) |

Example 27: Solubility Testing and Various Formulations of Compounds 118, 5 or 82 for Oral Dosing Compounds 118, 5 and 82 or poorly soluble in water as the free acid. They are however, soluble in DMSO, acetone and methanol. If one is unable to utilize these solvents then emulsion or suspension formulations may be an option as their free acids or salts. Compounds 118, 5 and/or 82 have been formulated as a suspension in 0.5% methylcellulose in Examples 15-20. They have also been formulated as solutions with various percentages of DMSO in water in Examples 22-24. Formulations using reduced particle size and increased homogeneity may provide potential for improved dissolution as well as control of batch reproducibility. Emulsions can be dosed in soft gel capsules. The compounds can be formulated as a salt. Example 9 presents a case of forming a sodium salt. Usually you need 2 pH units difference between acid and base pKa.

One can use a carrier or excipient to help with forming a suspension or solution of the compound for oral dosing. Some of these common excipients are listed in Table 12 and the range for early formulations.

What is claimed is:

1. A method for reducing caspase 3 levels for treating Amyotrophic Lateral Sclerosis (ALS), Parkinson's disease (PD) and Alzheimer's disease (AD), the method comprising administering to a subject in need of such treatment an effective amount of a compound of Formula 118 or 5:

118

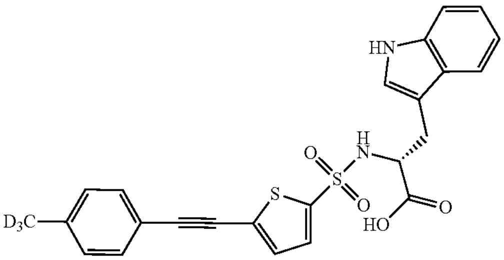

; or

-continued

5

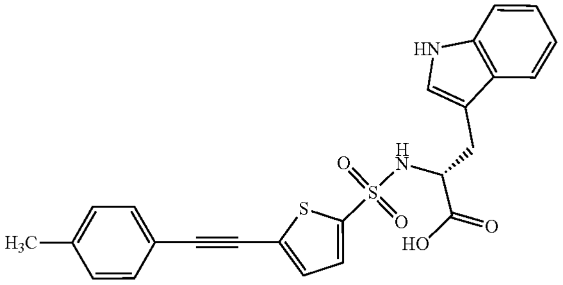

.

2. The method according to claim 1, wherein the administration is oral, rectal, topical, intravenous, parenteral, intraperitoneal, subcutaneous, intramuscular, ocular, transdermal, inhalative, nasal, sublingual, intraarticular, epidural and intrathecal.

* * * * *